United States Patent
Crump et al.

(10) Patent No.: US 8,378,811 B2
(45) Date of Patent: *Feb. 19, 2013

(54) MOBILE WIRELESS CUSTOMIZABLE HEALTH AND CONDITION MONITOR

(75) Inventors: Cindy A. Crump, Lovettsville, VA (US); Bruce G. Wilson, Williamsburg, VA (US); John Videtich, Holland, MI (US)

(73) Assignee: Aframe Digital, Inc., Lovettsville, VA (US)

( * ) Notice: Subject to any disclaimer, the term of this patent is extended or adjusted under 35 U.S.C. 154(b) by 564 days.

This patent is subject to a terminal disclaimer.

(21) Appl. No.: 12/568,116

(22) Filed: Sep. 28, 2009

(65) Prior Publication Data

US 2010/0016745 A1 Jan. 21, 2010

Related U.S. Application Data

(63) Continuation-in-part of application No. 11/371,071, filed on Mar. 9, 2006, now Pat. No. 7,616,110.

(60) Provisional application No. 60/660,342, filed on Mar. 11, 2005.

(51) Int. Cl.
*G08B 1/08* (2006.01)
*G08B 23/00* (2006.01)
*A61B 5/00* (2006.01)

(52) U.S. Cl. .......... 340/539.11; 340/539.12; 340/573.1; 600/301; 600/310; 128/903; 128/904

(58) Field of Classification Search ............ 340/539.11, 340/539.12
See application file for complete search history.

(56) References Cited

U.S. PATENT DOCUMENTS

| | | | |
|---|---|---|---|
| 5,416,695 A | 5/1995 | Stutman et al. | |
| 5,441,047 A | 8/1995 | David et al. | |
| 5,515,858 A | 5/1996 | Myllymaki | |
| 5,544,649 A | 8/1996 | David et al. | |
| 5,576,952 A | 11/1996 | Stutman et al. | |
| 5,807,267 A * | 9/1998 | Bryars et al. | 600/500 |
| 5,897,493 A | 4/1999 | Brown | |
| 5,997,476 A | 12/1999 | Brown | |
| 6,050,940 A | 4/2000 | Braun et al. | |
| 6,126,595 A | 10/2000 | Amano et al. | |
| 6,198,394 B1 | 3/2001 | Jacobsen et al. | |
| 6,224,548 B1 | 5/2001 | Gopinathan et al. | |
| 6,248,064 B1 | 6/2001 | Gopinathan et al. | |
| 6,252,883 B1 | 6/2001 | Schweickart et al. | |
| 6,292,698 B1 | 9/2001 | Duffin et al. | |
| 6,307,481 B1 | 10/2001 | Lehrman et al. | |
| 6,336,900 B1 | 1/2002 | Alleckson et al. | |
| 6,368,273 B1 | 4/2002 | Brown | |
| 6,375,614 B1 | 4/2002 | Braun et al. | |
| 6,402,691 B1 | 6/2002 | Peddicord et al. | |
| 6,416,471 B1 | 7/2002 | Kumar et al. | |
| 6,477,117 B1 * | 11/2002 | Narayanaswami et al. | 368/251 |
| 6,485,418 B2 | 11/2002 | Yasushi et al. | |
| 6,491,647 B1 | 12/2002 | Bridger et al. | |
| 6,501,386 B2 | 12/2002 | Lehrman et al. | |
| 6,516,289 B2 | 2/2003 | David | |
| 6,533,729 B1 | 3/2003 | Khair et al. | |

(Continued)

FOREIGN PATENT DOCUMENTS

WO 98/20439 5/1998
WO 03/008211 10/2003

*Primary Examiner* — Donnie Crosland
(74) *Attorney, Agent, or Firm* — Maier & Maier PLLC

(57) ABSTRACT

A wearable sensor may be provided. The wearable sensor may include a timing mechanism; a plurality of sensor pairs coupled to the timing mechanism wherein each sensor pair comprises an emitter and a detector; and a microcontroller coupled in communication to the timing mechanism and the plurality of sensor pairs.

22 Claims, 11 Drawing Sheets

U.S. PATENT DOCUMENTS

| | | |
|---|---|---|
| 6,537,225 B1 | 3/2003 | Mills |
| 6,540,673 B2 | 4/2003 | Gopinathan et al. |
| 6,544,173 B2 | 4/2003 | West et al. |
| 6,575,912 B1 | 6/2003 | Turcott |
| 6,595,918 B2 | 7/2003 | Gopinathan et al. |
| 6,608,562 B1 | 8/2003 | Kimura et al. |
| 6,659,947 B1 | 12/2003 | Carter et al. |
| 6,749,566 B2 | 6/2004 | Russ |
| 6,864,796 B2 | 3/2005 | Lehrman et al. |
| 6,921,367 B2 | 7/2005 | Mills |
| 6,968,375 B1 | 11/2005 | Brown |
| 7,616,110 B2 * | 11/2009 | Crump et al. ............ 340/539.11 |
| 2003/0107487 A1 * | 6/2003 | Korman et al. ............ 340/573.1 |
| 2004/0111045 A1 | 6/2004 | Sullivan et al. |
| 2004/0228217 A1 * | 11/2004 | Szeto ............................. 368/11 |
| 2006/0031934 A1 | 2/2006 | Kriegel |

\* cited by examiner

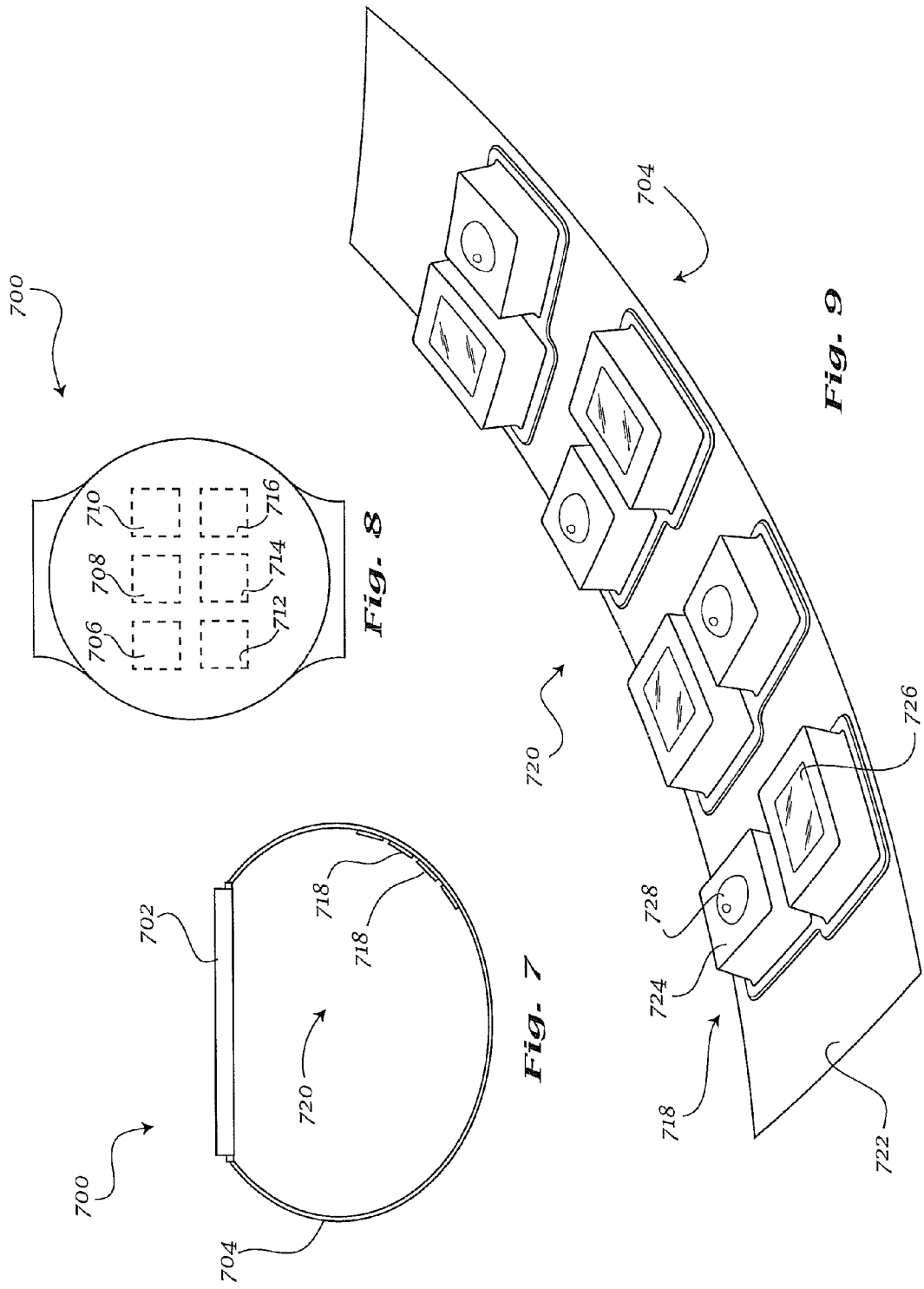

MOBILE WIRELESS CUSTOMIZABLE HEALTH AND CONDITION MONITOR

CROSS-REFERENCE TO RELATED APPLICATIONS

This application is a continuation-in-part of U.S. patent application Ser. No. 11/371,071, filed Mar. 9, 2006 now U.S. Pat. No. 7,616,110, and entitled MOBILE WIRELESS CUSTOMIZABLE HEALTH AND CONDITION MONITOR, which claims priority under 35 U.S.C §119 to U.S. Patent Provisional Application No. 60/660,342, filed Mar. 11, 2005. The disclosures of the above-referenced applications are incorporated by reference herein in their entireties.

BACKGROUND OF THE INVENTION

Nursing homes and assisted care facilities employ a number of different methods and devices to monitor their patients. These devices are capable of monitoring physiological functions, but are generally used in isolation and not integrated with other devices. Some devices include fall alert buttons that require a patient to actively push a button to alert the staff of a care facility of a fall. This type of device, however, is not effective for a patient who has a cognitive impairment (such as dementia) is knocked unconscious or otherwise rendered incapacitated by a fall or other medical condition. Care facilities also use a variety of pressure pads and other sensors to provide an audible alert to indicate that a patient has left a desired location. These types of devices have reliability problems and require a high level of vigilance to constantly monitor the sensors. Moreover, none of these devices is capable of delivering private, targeted and configurable alerts for designated caregivers, nor do they provide centralized data collection for automatic charting and close monitoring of individual patients.

In addition to the above, many care facilities try to perform at least some vital sign monitoring. This may be limited to checking a patient's vital signs only once a week due to the time and cost required to have staff to perform these duties. However, when a patient's vital signs are checked only once a week, the declining health of a patient may only be detected after a health condition has worsened, eliminating the opportunity for early intervention. Thus, there can be an increase in a care facility's patient morbidity and mortality rate. Additionally, staff turnover and productivity can be an issue in care facilities that may need to spend more time replacing and training staff members to monitor sensors and patients' vital signs and to understand the patient's medical history and specific need for care.

Care facilities also have an interest in knowing the location of their patients at their facility, as well as patients that may be located remotely or living at individual homes and receiving care remotely. However, typical methods of monitoring patients and determining their locations involve the use of video cameras and closed-circuit television. Another method is the use of motion detectors to infer movement and activity level within a home. These systems typically require significant wiring or installation of equipment within a home and can be uneconomical for either home or multi-patient facility use. Moreover, motion detectors cannot distinguish between multiple residents or pets present in the home. Additionally, this may only provide an inference, but not a direct and objective indication, of the patient's well-being. Further, video-based services require a high level of attention to the video feeds from the cameras and the identity of the people can be difficult to discern. There are additional issues in personal privacy and intrusion when using video or even motion detectors. Additionally, it is not usually practical to have cameras or a video monitoring system in the house of a remotely located patient.

Other facilities, such as hospitals, have also utilized patient and personnel tracking systems using radio frequency identification (RFID) badges. These devices can be worn by a person and may be passive devices or may transmit an RF signal that may be tracked from a centralized location in the facility. These devices, however, do not provide any other information besides the location of the wearer and they may not provide adequate transmission range. Also, RFID is limited in its memory so very little processing is available and there is no 2-way processing of event monitoring data. Other information that a care facility may desire to collect, such as a patient's vital signs, are not collected or transmitted by these devices. Additionally, the battery life on these devices can vary significantly depending on the type of RF signal transmitted and the amount and duration of transmissions from the device. Typically the devices only have a battery life of a few hours or several days before they require recharging or replacing the batteries. Other devices designed to transmit a signal having information about a patient may utilize cellular phone technology. These devices, however, often fail to get an appropriate cellular signal inside health care facilities and again require significantly more power and have a battery life of hours thereby rendering such devices impractical for long-term monitoring.

Yet other devices that have been used in battery-powered sensors include those using IEEE 802.15.1 Bluetooth wireless technology to replace cables. Enabling devices with Bluetooth does not in itself bring about an integration of separate monitoring devices for one patient. Indeed, there can be a limit of eight devices that may be joined together in a Bluetooth pico-net raising the question about scaling and the capacity to support hundreds of patients in a facility. The short range, typically on the order of ten meters, calls for a multi-mode extensive network strategy to support a healthcare facility, such as a mesh or partial mesh network, would provide for adequate coverage but also exceeds the specifications of Bluetooth. Merely replacing a cable from a monitor to a wireless Bluetooth-enabled equivalent can result in rapid battery depletion if continuous monitoring is attempted.

Still other devices have been used for monitoring an individual's vital signs. These devices have been wearable and typically were capable of monitoring some vital signs, such as pulse rate and body temperature. These devices, however, typically only have the ability to display the information collected on a display that is either worn on the individual or on separate display that the collected data is downloaded onto. Some devices that monitor vital signs, such as pulse rate, require the patient to be relatively still to obtain an accurate reading. Other devices have included the ability to transmit location information to track the movement of an individual. These devices, however, do not have the ability to transmit collected data on the individual back to a central location for analysis. Further, these devices usually require a person to wear a variety of different sensors and can be intrusive on the person, embarrassing to wear, and prohibit some movement. These devices also only allow a person to wear the device for a limited time, for example a few hours to several days, before the power source must be replaced or recharged.

Therefore, a need exists for a system that can track and monitor a patient using a wearable, form-friendly, low-power, wireless device that can be used to monitor the health and wellness of a person wearing the device during the person's daily activities, over long periods of time without the need to recharge the device, and without the constant surveillance of healthcare personnel.

BRIEF DESCRIPTION OF THE INVENTION

In one exemplary embodiment, a wearable sensor may be provided. The wearable sensor may include a timing mechanism; a plurality of sensor pairs coupled to the timing mechanism wherein each sensor pair comprises an emitter and a detector; and a microcontroller coupled in communication to the timing mechanism and the plurality of sensor pairs.

In another exemplary embodiment, a monitoring system may be provided. The monitoring system may include at least one wearable monitor coupled to a user, the at least one wearable monitor may include a timing mechanism; a plurality of sensor pairs coupled to the timing mechanism wherein each sensor pair comprises an emitter and a detector; and a microcontroller coupled in communication to the timing mechanism and the plurality of sensor pairs; at least one gateway having a second transceiver; at least one device located at a remote location; and at least one server coupled in communication using a wide area network to the at least one gateway and the at least one device, the at least one wearable monitor is coupled in wireless communication to the at least one gateway, the plurality of sensor pairs facilitate sensing a heart rate of the user and transmit the heart rate to the at least one server.

In yet another exemplary embodiment, a method may be provided of sensing a heart rate using a wearable monitor that includes a timing mechanism, a memory, a plurality of sensor pairs coupled to the timing mechanism wherein each sensor pair includes an emitter and a detector, and a microcontroller coupled in communication to the timing mechanism, the memory and the plurality of sensor pairs. The method may include coupling the wearable monitor to a user; emitting an electromagnetic wave from the emitter into the user; receiving an electromagnetic wave signal from the user at the detector; stabilizing the electromagnetic wave; determining a first pulse; determining a plurality of subsequent pulses; calculating a heart rate of the user; and recording the heart rate of the user in at least one server.

In yet another exemplary embodiment, a health care monitoring system may be provided. The health care monitoring system may include means for emitting electromagnetic waves into a user; means for receiving the emitted electromagnetic waves as a signal; means for determining a plurality of peak amplitudes within the signal; means for calculating a heart rate of the user; and means for recording the heart rate on at least one server.

BRIEF DESCRIPTION OF THE DRAWINGS

Advantages of embodiments of the present invention will be apparent from the following detailed description of the exemplary embodiments. The following detailed description should be considered in conjunction with the accompanying figures in which:

FIG. 7 shows a side view of an alternative monitor that may be used with the system shown in FIG. 1;

FIG. 8 shows a bottom view of the monitor shown in FIG. 7;

FIG. 9 shows a perspective view of a band that may be used with the monitor shown in FIG. 7;

DETAILED DESCRIPTION OF THE INVENTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Referring generally to FIGS. 1-6, a medical situation awareness system that can monitor the health, location or well-being of a person is shown. The system may include a user-friendly, internet-based interface and tools for analyzing data. The system may also include a scalable, customizable database for management and codification of the uncertain relational knowledge gathered regarding multiple data types that may be collected about the person. This database can include advanced analytic tools. Additionally, the system can include a Bayesian advanced analytic software tool that can take the uncertain relational knowledge gathered and develop a Bayesian relational network. This network may then be used to create a predictive model of medical condition for the monitored patient. The model may be used, for example, to filter false positives, incorrect data or inaccurate data. This may be accomplished by including other data types that correlate in a health model. This autonomic process could allow for an effective wearable monitoring system because the event data from the sensors could require significant analysis time by an operator to ensure an accurate picture of the patient's overall health is provided. Further, the system may have a graphical interface that can be used for results analysis or health care suggestions. This system may be employed in any of a variety of situations, for example hospitals, extended care facilities, nursing homes, private homes, or any other situation where it is desirable to monitor and provide care for a person.

Figure 1:
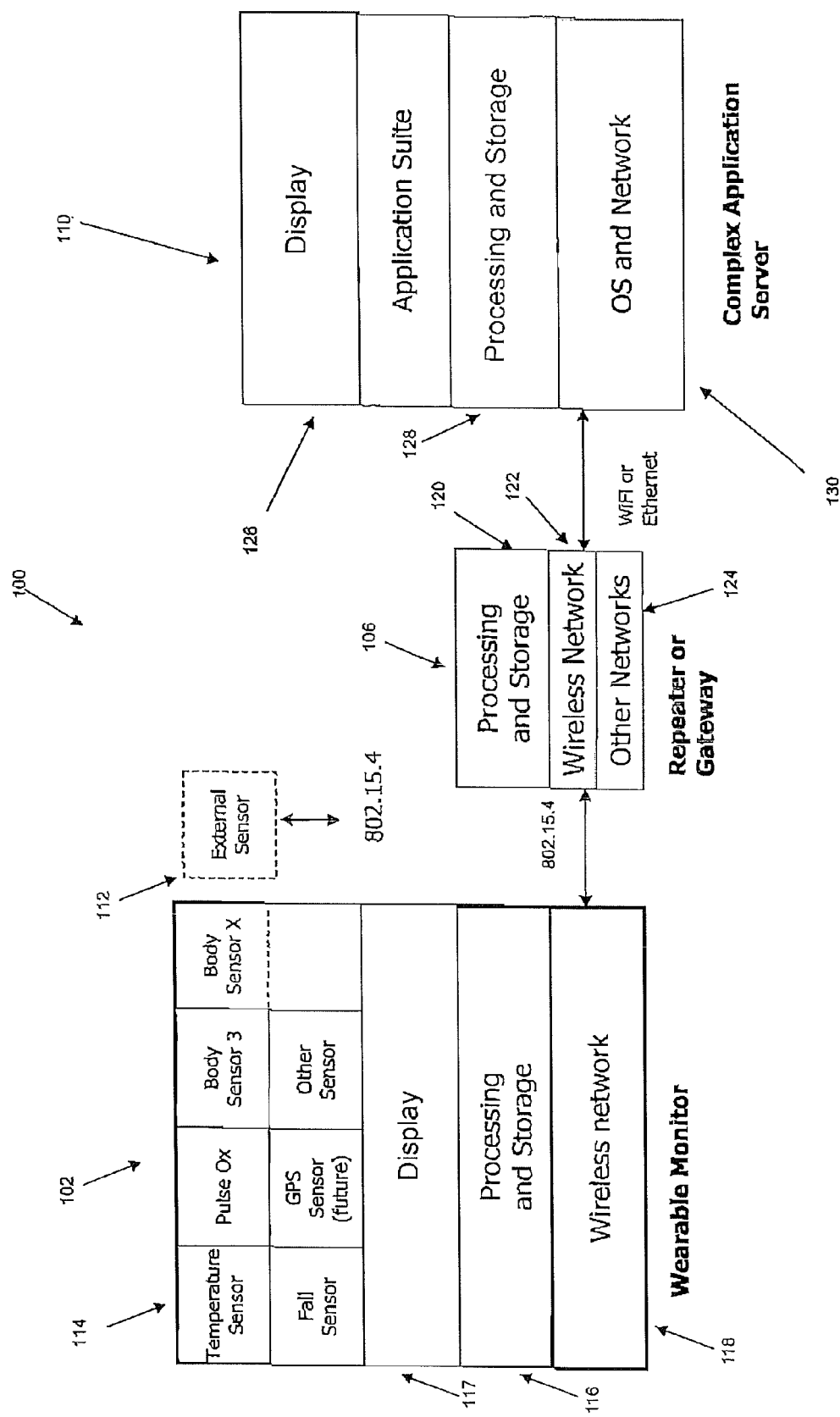
FIG. 1 shows an exemplary diagram of a health care monitoring system.

FIG. 1 shows an embodiment of a health care monitoring system. System 100 may have a variety of components, such as monitor 102, gateway 106 and server 110. Monitor 102, gateway 106, and server 110 may transmit data to each other and receive data from each other through any of a variety of wireless transmission protocols. Further, monitor 102 may include sensors 114 to detect physiological, locational and other data from a wearer of monitor 102. These sensors may include, but are not limited to a temperature sensor, a pulse oximetry sensor, a variety of body sensors, a fall detection sensor, and a location sensor, as well as any of a variety of other sensors. Additionally, external sensor 112 may be disposed separately from sensors 114 to detect and transmit data from a location apart from monitor 102. Monitor 102 may further include processing and storage capabilities 116 for processing and storing the data from the sensors as well as data received from outside sources. Monitor 102 may also include display 117 for facilitating communication to the patient of patient reminders and messages from server 110 or gateway 106. Also, mesh network 118 may be utilized with monitor 102. Mesh network 118 may include a variety of repeaters so as to allow for the transmission of data over significant areas as well as for use in providing location information of a wearer of monitor 102.

Gateway 106 can communicate wirelessly with monitor 102 and server 110 and may also include processing and storage capabilities 120, which may be able to process and store data transmitted from monitor 102, as well as data generated by gateway 106 and data received from server 110. Gateway 106 may be part of a wireless local area network (LAN) 122 and also part of other networks 124, allowing it to communicate with other devices, for example, over the Internet.

Server 110 may communicate with gateway 106 over network 130 to both send and receive data. Server 110 may include processing and storage capabilities 128, which may be used for processing, interpreting and storing data received from gateway 106 and monitor 102, as well as performing other analyses, such as eliminating false alarms and predicting future events. Further, server 110 can include a display 126, such as a nurse's display, where a person may access the data stored and processed by server 110.

Figure 1A:
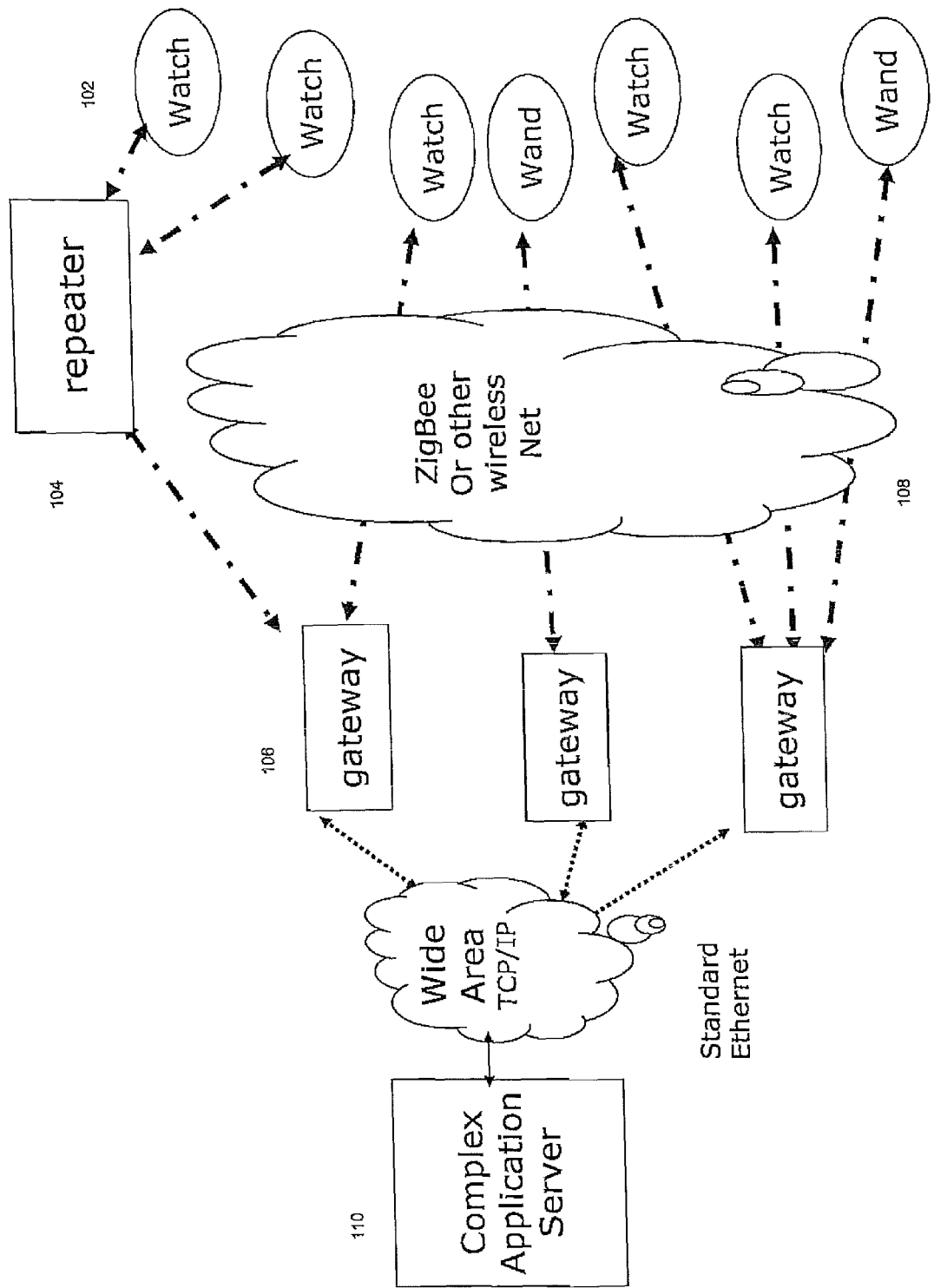
FIG. 1a shows an exemplary diagram of a health care monitoring system.

In another embodiment shown in FIG. 1a, a system 100 for monitoring the health, location or well-being of a person is shown. Here, a person may use a device such as a wearable monitor 102. The monitor 102 can be a hardware device taking the form of an arm band or a wrist band or a device that can be applied to the skin via a bandage, as a non-limiting example. In a further embodiment, the monitor 102 can be wearable and not interfere with any range of motion or actions of a person. The dimensions of the monitor 102 may also be small, for example, 1"×1"×3" or smaller. There may be a variety of sensors, such as a pulse sensor, temperature sensor and a mobility sensor, integrated into the monitor 102, as a few non-limiting examples. Further, a panic button may be disposed on the monitor 102, allowing a wearer or other person to send a signal to a remotely located party, such as a caregiver or a facility's server. Additionally, the monitor 102 may incorporate "fall detection," which can detect if a person falls down or otherwise moves in a manner that could result in an injury. The fall detection may use any of a variety of sensors, alone or in combination, for example, piezoelectric-based, accelerometer-based and gyroscopic-based. The sensor or sensors may be incorporated in the monitor 102 whether it is worn on a wrist of a patient or anywhere else on their body. Further, the fall detection portion of the monitor 102 can send also send a signal to a caregiver or a facility's server.

In an additional embodiment of the monitoring system, the wearable monitor 102 can send a wireless signal to a repeater 104. The repeater 104 can be a custom hardware device that may be battery or AC powered. The repeater 104 may also be installed in any location where additional routing nodes may be required, to provide further wireless coverage and allowing the wearable monitor to communicate with a smart gateway.

Further, in the system shown in FIG. 1a, a smart gateway 106 may be utilized to further transmit a wireless signal. In one exemplary embodiment, the smart gateway 106 may be a hardware device that integrates IEEE 802.15.4 ZigBee wireless networking components with Ethernet, 802.11 wireless routers or a modem. IEEE 802.15.4 may be used as it allows a large number of nodes to join the network, thus permitting a large number of patients to be monitored. Communication may occur over the 2.4 GHZ band, which is unlicensed and available in most locations, allowing for a single product to be utilized throughout the world. Additionally, to avoid congestion caused by other devices using this band, the IEEE 802.15.4 ZigBee standard may use 16 channels in the 2.4 GHz band, allowing the monitor 102 to utilize less crowded channels when necessary. Likewise, any spectrum, which may be licensed for the purpose of monitoring or may be not licensed, such as the 5 GHz spectrum, may be used to avoid potential interference with other devices. Also, because 802.15.4 has a relatively long range, larger scale monitoring can occur. This transmission protocol is also a very low power protocol, allowing for extended use of the monitors, and the low data rate and limited interference with other devices allow for 802.15.4 devices to work in environments where other RF devices are already operating. However, in other exemplary embodiments, any other type of wireless networking devices, components or protocols may used with the gateway 106. The gateway 106 can collect the event data generated by the wearable monitor and may send real-time medical alerts directly to a caregiver or, alternatively, to a facility's server for further analysis and action.

Although the above embodiments discuss the IEEE 802.15.4 ZigBee wireless standard, any wireless communication protocol known by a person of ordinary skill in the art could be used for transmitting and receiving. In another embodiment, any wireless communication protocol known to a person having ordinary skill in the art that has economical power consumption, reasonable data rates, limited interferences, and sufficient range may be used.

After the wireless signal shown in FIG. 1a is transmitted from the smart gateway 106, it can pass through a local area network 108 to a server 110. The server 110 can be a software application that allows a nursing home facility or other care giving facility to track the incidence of fall reports, medical emergencies and other transmissions of the wearable monitor at their site. The server 110 can also have the ability to send targeted real-time medical alerts to facility employees and can escalate these alerts to various members on the staff, as well as track response times, for example, to the medical alerts. The server 110 may also provide statistics on the vital signs of the residents as well as the location of the residents. Further, the server 110 may be able to perform intelligent analyses of event data, and of multiple correlating data types in health models created by the system, to minimize false alarms and allow for predictive decision support of healthcare providers, which could lead to improved care. Data transmitted to the server 110 may be forwarded to any of a variety of devices 112, and be viewable over the Internet or a local area network. The data may then be reviewed and analyzed by an authorized person at the remote location of the device 112.

In yet another embodiment, the system 100 may be used in either a health care facility or at an individual's home. Further, a monitor 102 that functions in a health-care facility may also change locations to the individual's home or another location that is compatible with the system. Additionally, if the user moves back to the original care facility, the monitor 102 can continue to work seamlessly. Further, the same equipment for system 100 that is used in a health-care facility may be used for a patient at their home, as the equipment is typically relatively inexpensive. The message protocols used in the system can provide end-to-end integrity and security in the data from each wearable monitor and each sensor as the data is transmitted over wireless networks to the Internet or public carrier networks to reach the server having patient's records.

Figure 2:
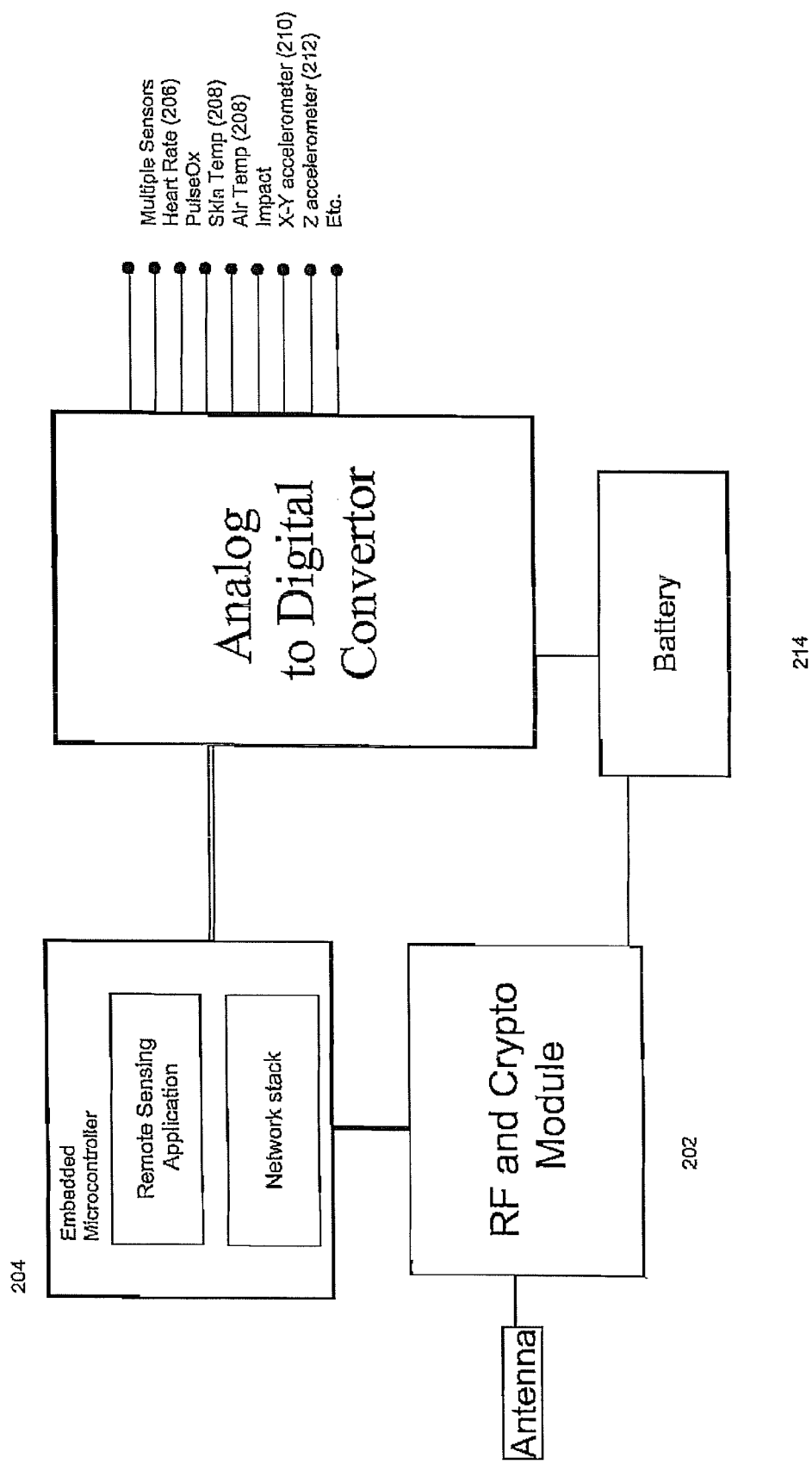
FIG. 2 shows an exemplary diagram of a wearable monitor.

FIG. 2 shows a more detailed diagram of the wearable monitor 102. The monitor 102 may be used to monitor the health and mobility of the wearer. In one embodiment, the monitor 102 may be a low-cost, high volume device that can be replaceable if it is lost or broken. The monitor 102 may also be customized based on whether or not it is being used in a wearer's home or at a care facility. The monitor 102 can include a wristband device, which may be a physically attractive, compact device capable of being worn on the wrist, similar to a wrist watch. Alternatively, the wearable monitor 102 may be a pager-sized device that can be attached to the belt of a wearer or to an armband or leg-band on the wearer. In yet another embodiment, the wearable monitor 102 could be formed so that it is integrated in a bandage or similar adhesive device that may be securely worn anywhere on the body of a wearer.

Although some embodiments have been described as including a wrist watch or pager-sized device, or the same divided into two or more smaller pieces, or any configuration known to one having ordinary skill in the art that would attach to the body securely and not inhibit or intrude upon the mobility, nor limit the range of motion of a user may be used. A version of the wearable monitor called a "wand" may be carried by authorized healthcare and support personnel. The wand can function to communicate with the server or other system components to verify patient identity, verify proper operation of the patient's wearable monitor, verify that the healthcare personnel have responded to medical alerts and notifications made by the system and have attended to the needs of the patient, as well as verify or determine any other relevant information.

The monitor 102 may have a variety of internal components, regardless of whether the wearer has the wristband device or the pager-sized device. An 802.15.4 wireless transceiver 202 may be disposed in the monitor. Alternatively, another wireless transceiver may be used with monitor 102. Additionally, an antenna can be disposed in the device. The antenna may be able to produce a significantly uniform signal having a significantly uniform signal strength emanating to all directions (substantially isotropic) regardless of the orientation of the monitor due to change in position of the wearer of the monitor. The antenna may further be optimized for communication in an indoor environment. A processor 204 may also be housed in the device. In an exemplary embodiment, the processor 204 can be an ultra-low power 8-bit processor. Additionally, a processor 204 may be utilized that has a hibernate mode where only micro-amps of current are used to power the hibernating device, and which only "wakes up" or activates to process events which can minimize power requirements and extend battery life. Flash memory (not pictured), or any type of solid-state memory known to one having ordinary skill in the art, may also be employed in the monitor 102. The flash memory can contain the latest sensor data and alerts when the wearable monitor is out of the range of a network, the protocol stack as well as firmware developed to react to events generated by the sensors.

In addition, the monitor can include any of a variety of sensors. These sensors can include medical-grade sensors which can be employed to determine the health of the wearer. For example, the sensors may include a pulse sensor 206, a temperature sensor 208 and accelerometers for the x-y axis 210 and z axis 212, allowing for mobility detection and fall detection. Further the mobile device can include a battery or batteries 214. The battery or batteries 214 may be such that they allow for the device to run off of the battery power for more than six months. Any of a variety of batteries may be used in both the wristband and pager-size applications. The battery or batteries 214 may also be any of a variety of rechargeable batteries, and may therefore reduce the need for replacing battery or batteries 214.

Further embodiments of the monitor 102 not pictured in FIG. 2 may include a blood pressure sensor, a pulse oximetry sensor (to provide more accurate blood oxygen saturation determination mechanisms), a temperature sensor, respiratory rate sensor, wireless network-based location sensor and GPS or cell-based geo-location and E911 service. Further embodiments of the monitor 102 not pictured in FIG. 2 may include sensors for military, hazardous or similar applications, for example a blast pressure sensor or a bio-contagion sensor. Individual sensors may be utilized to monitor these events or a single sensor may be utilized to perform a one or more of the tasks. Additionally, a shock meter that may use galvanic skin resistance and skin temperature, along with event analysis software to provide an early detection of shock may be incorporated.

Although the above preferred embodiments discuss a blood pressure sensor, laser pulse oximetry sensor, a temperature sensor, respiratory sensor, GPS and E911 services, any other sensor or service known to one having ordinary skill in the art may be used or incorporated into the device.

The wearable monitor 102 can use wireless networking components in order to send vital sign data, location information and medical emergency alerts. In one exemplary embodiment, 802.15.4 ZigBee wireless networking components (e.g. transceiver 202) may be used. In another exemplary embodiment, any other wireless networking components may be used that may be disposed on monitor 102 and provide for transmitting and receiving data wirelessly. Additionally, the monitor 102 can incorporate GPS locating capability to provide detailed location information of the wearer. Further, a cellular modem may be incorporated onto the monitor 102, allowing the wearer to be monitored from remote locations and, optionally, interacting with ZigBee or equivalent-enabled mobile phones.

The software that can be used in the wearable monitor 102 can be designed to be small, thus limiting the amount of processing power required and therefore extending battery life. Additionally, the software incorporated on the monitor 102 can be programmed into firmware. One portion of the software can include an IEEE 802.15.4/ZigBee protocol stack or any alternative wireless protocol stack. This combination can provide the ability for the wearable monitor 102 to wirelessly communicate with one or more repeaters and gateways. Additionally, in one embodiment, since the wearable monitor 102 may require very low power consumption, it can be considered an end node that does not route data, and thus may be considered a reduced function device (RFD) under the IEEE 802.15.4 standard. However, in other embodiments, the monitor 102 can have full routing functions and utilize any known wireless standard. Further, the software may also be able to respond to beacons or directed messages from a gateway device that is requesting current sensor data to be sent. Also, in a further embodiment, the data transmitted from the wearable monitor 102 can be encrypted, for example, using the security capabilities of the 802.15.4 standard or any other Advanced Encryption Standard (i.e. AES 128 or AES 256) scheme known to one of ordinary skill in the art may be used.

Additional software may be used for processing sensor data and ensuring that out of range data is processed for all of the sensors that are integrated into the device. For example, in the case of fall detection, the software should be able to process the data and determine if a fall has occurred or if a typical movement has occurred. Also, sensor data may be time stamped, gathered and sent to a gateway on a periodic basis for statistical tracking of norms. In a further embodiment, if there is a network failure, data or high-water mark sensor data can be latched and transmission can be retried until transmission is confirmed. Additionally, the wearable monitor 102 can also test battery power of battery 214 on a regular basis and may also transmit a "low battery" alert when battery life has decreased below a predetermined amount, for example, 20% of the remaining battery life. Alternatively, a "low battery" alert may be transmitted at any predetermined amount at or below 50% of the remaining battery life.

Figure 3:
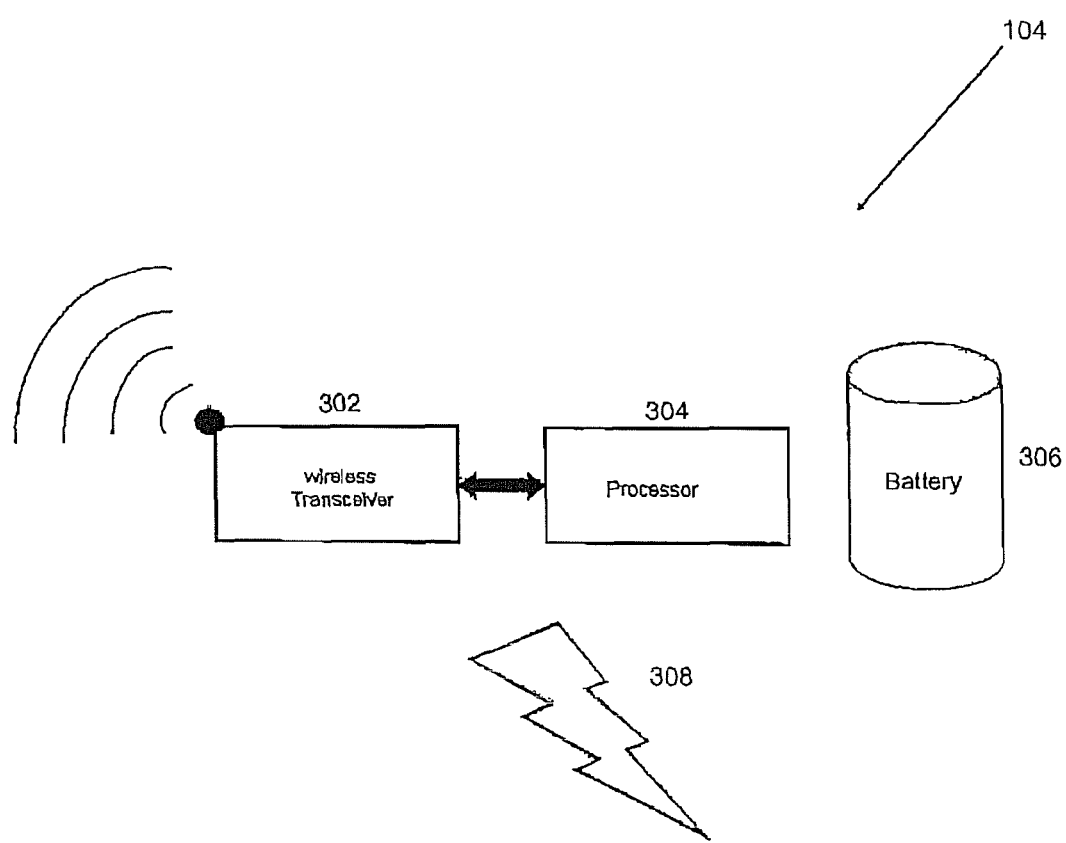
FIG. 3 shows an exemplary diagram of a repeater.

An exemplary repeater is shown in FIG. 3. A repeater 104 can ensure that adequate wireless coverage is maintained across the facility or home where the wearer of the monitor is located. In one embodiment, a repeater 104 can collect the statistics and alerts generated by the wearable monitor 102 and transmit real-time medical alerts to a caregiver or a care facility's server. Increasing the number of repeaters, for example in a mesh pattern or any other pattern known by one of ordinary skill in the art that will provide the desired coverage, in a given location, can also reduce the number of gateways that a home or facility may need. Additionally, the number of repeaters may be increased to support a virtually unlimited number of monitored patients and, additionally, determine the location of any individual patient. Repeaters can also compensate for the signal sent from an ultra-low power wearable monitor, which may have a limited transmission range. The repeater 104 can use a variety of hardware and software and may be changed or customized depending on the type of repeater that is being used. Non-limiting examples of different repeaters include an internal-use-only repeater that is A/C powered with battery backup, an internal-use-only repeater that is D/C battery powered, a weatherproof repeater that is A/C powered with battery backup, and a weatherproof repeater that is D/C battery powered.

A repeater 104 may also utilize a variety of internal hardware components, as shown in FIG. 3. With the exception of the A/C power transformer in the A/C power devices, the hardware configurations for different repeaters may all be the same. The repeater can house an 802.15.4 wireless transceiver 302 that meets both the size and power requirements of the device. The 802.15.4 transceiver 302 may be further integrated with an Ethernet connection, one or more 802.11 wireless Internet routers and one or more dial-up modems (not shown). In other embodiments, the repeater 104 may house any other type of wireless transceiver. Additionally, the repeater 104 can have an antenna, which may be customized or altered depending on whether or not the monitor is being used indoors or outdoors. Further, the repeater 104 may also have an ultra-low power 8-bit processor 304, similar to the one described above with respect to the monitor and optionally having a hibernate mode. Additionally, the repeater 104 can utilize flash memory containing the protocol stack as well as firmware developed to react to repeater events, a battery or batteries 306, which may power the repeater for one year or longer and an A/C power transformer 308, which can be utilized for locations with an electrical plug.

The repeater 104 may also have a software component designed to be small to limit the amount of processing power and thus extending the battery 306 life in the event that the device is not A/C powered. This software may be entirely programmed into the firmware. One part of the software may be the IEEE 802.15.4/ZigBee protocol stack, or any other appropriate wireless protocol stack, which can provide the ability for the repeater to wirelessly communicate with wearable monitors and gateways in the system. The repeater 104 can be designed as a routing node, allowing it to pass data along from source nodes to destination nodes. The repeater may also be considered a full function device (FFD) in terms of the IEEE 802.15.4 standard. The repeater 104 further may utilize any of a variety of batteries, for example type N or rechargeable batteries, to power it as it routes data or may alternatively be A/C powered. Finally, the software on the repeater 104 may also respond to beacons from a gateway device, which can request current status to be sent. The status data transmitted from the repeater 104 to a gateway device can include both status data of the repeater 104 itself as well as current status data of the wearer of the monitor 102. If the repeater 104 is battery powered, additional processing may be performed that tests the battery power on a regular basis and sends a low battery alert when a predetermined amount of battery power in battery or batteries 306 is, for example 20%. Alternatively, a "low battery" alert may be transmitted at any predetermined amount at or below 50% of the remaining battery life.

Figure 4:
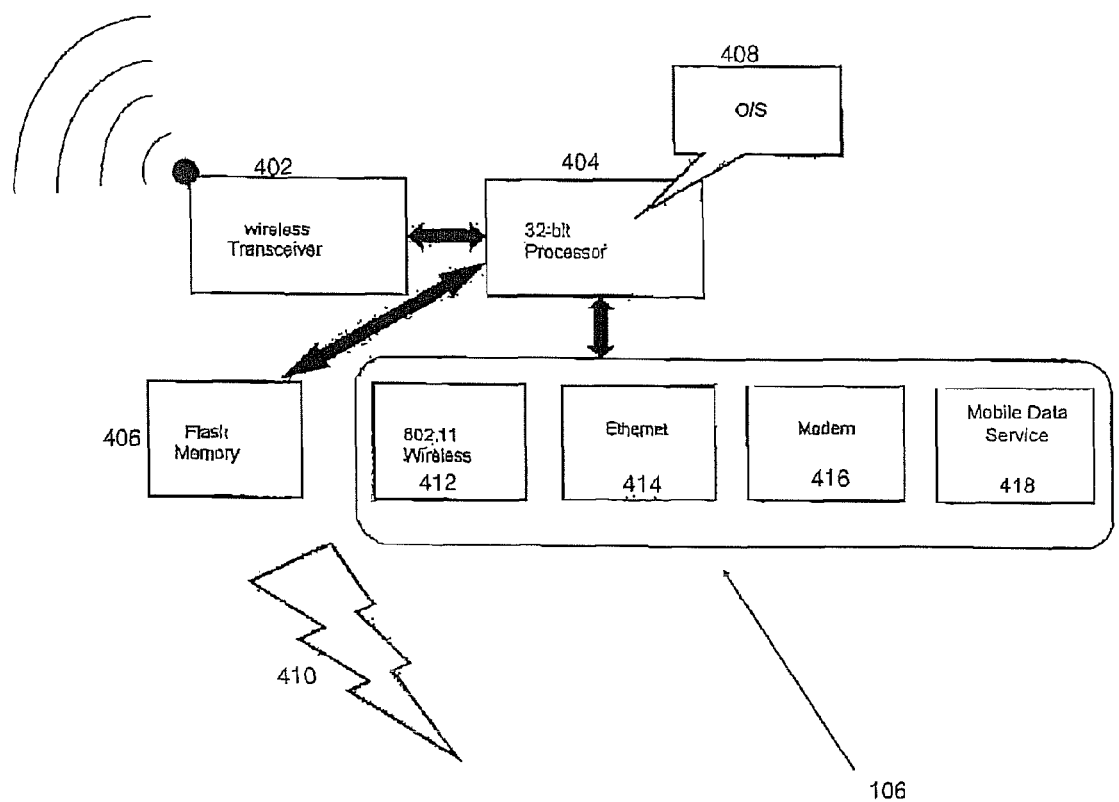
FIG. 4 shows an exemplary diagram of a gateway.

An exemplary gateway device, as shown in FIG. 1, item 106, is shown in greater detail in FIG. 4. The gateway device 106 can be a fixed-location device that bridges a 802.15.4 ZigBee wireless network, or any other alternative wireless network used by the above-described devices, with a local area network in a facility or home. A variety of wearable monitors 102 and repeaters 104 may operate through an individual gateway 106 and the gateway 106 may have similar functionality to an 802.11 wireless access point, or any other type of wireless access point. Similar to the repeater 104, the gateway 106 may utilize a variety of hardware and software components. Additionally, the gateway 106 may have different configurations based on the local area network 108 that is configured in a facility or home. For example, a gateway 106 may be an A/C powered device with Ethernet network connectivity, an A/C powered device with 0.802.11b (or other) network connectivity, or an A/C powered device with modem connectivity.

In a further embodiment shown in FIG. 4, a gateway 106 may have a variety of hardware components. These components may include an 802.15.4 wireless transceiver 402, or any other type of wireless transceiver, and an antenna, similar to those in the repeater 104. The gateway 106 may also have a processor 404, for example a 32-bit processor. Additionally, the gateway 106 can utilize flash memory 406, or other memory type, which can store patient data as a temporary network buffer and contain the protocol stack as well as firmware message processing 408. The gateway 106 can also have an amount of RAM that is needed for the application and an A/C power transformer 410 to provide power for the gateway, as well as an internal D/C battery backup.

The gateway 106 may also provide Internet connectivity. Connections to the Internet may be made by at least one of an 802.11 wireless connection 412, Ethernet connection 414, modem 416, cellular or mobile data service 418, or any other device capable of connecting to the Internet.

The software used in the gateway 106 shown in FIG. 4 can be used in processing events from the wearable monitor and may optionally be Linux-based. Additionally, all of the software incorporated into the gateway may be programmed into the firmware. One such software component is an operating system, for example a Linux or Linux-variant operating system 408. Further, the gateway 106 can include an IEEE 802.15.4/ZigBee protocol stack, or any other type of wireless protocol stack, the combination of which can provide the ability for the gateway 106 to wirelessly communicate with wearable monitors 102 and repeaters 104 in the system 100. The gateway 106 may further be designed as a routing node so that it can pass data along from source nodes to destination nodes. The gateway 106 may be considered a personal area network (PAN) coordinator node under the terms of the IEEE 802.15.4 or master node under IEEE 802.15.1 or other wireless standard. Additionally, if there are multiple gateways in the network for scalability, a single gateway may be chosen as the PAN coordinator and the remaining gateways can function as coordinators in a cluster tree network topology. The coordinator nodes can also generate beacons, for example status requests, that the other nodes in the network may respond to on a periodic basis.

Other software included in a gateway 106 can include a reliable queue, which can provide for scalability and reliability of the delivery of critical monitoring events to the server, as well as delivery of critical confirmations and messages from the server to monitors 102. A gateway 106 can also have the capability to process the events sent to it by the wearable monitors 102 and the repeaters 104. In situations where there may be multiple events from the same monitor 102 or repeater 104, the gateway 106 can have the intelligence to collapse the events and perform a root cause analysis. Finally, gateways can receive software upgrades and updates. Further, gateways may be able to upgrade the wearable monitor and repeater components when new firmware is made available for updates.

In another embodiment, the system may be utilized in the home of a patient. A home-based system, however, may contain a gateway 106 having additional intelligence so that it also can have the decision making capabilities based on a patient's physiological trends and statistical data for instances where a patient can be provided immediate feedback for self awareness and patient education about their ailments. A home based system may also contain repeaters 104 serving as locating nodes and providing daily activity assessment data regarding the patient. The gateway device 106 may also be able to continue communication with a healthcare provider's server 110 so that a healthcare team can maintain their ability to monitor the patient. The communication between the system in the patient's home and the healthcare facility can be securely delivered through encryption to ensure patient privacy and, if necessary, to comply with the Health Insurance Portability and Accountability Act (HIPAA) regulations and, if necessary, military specific requirements.

Figure 5:
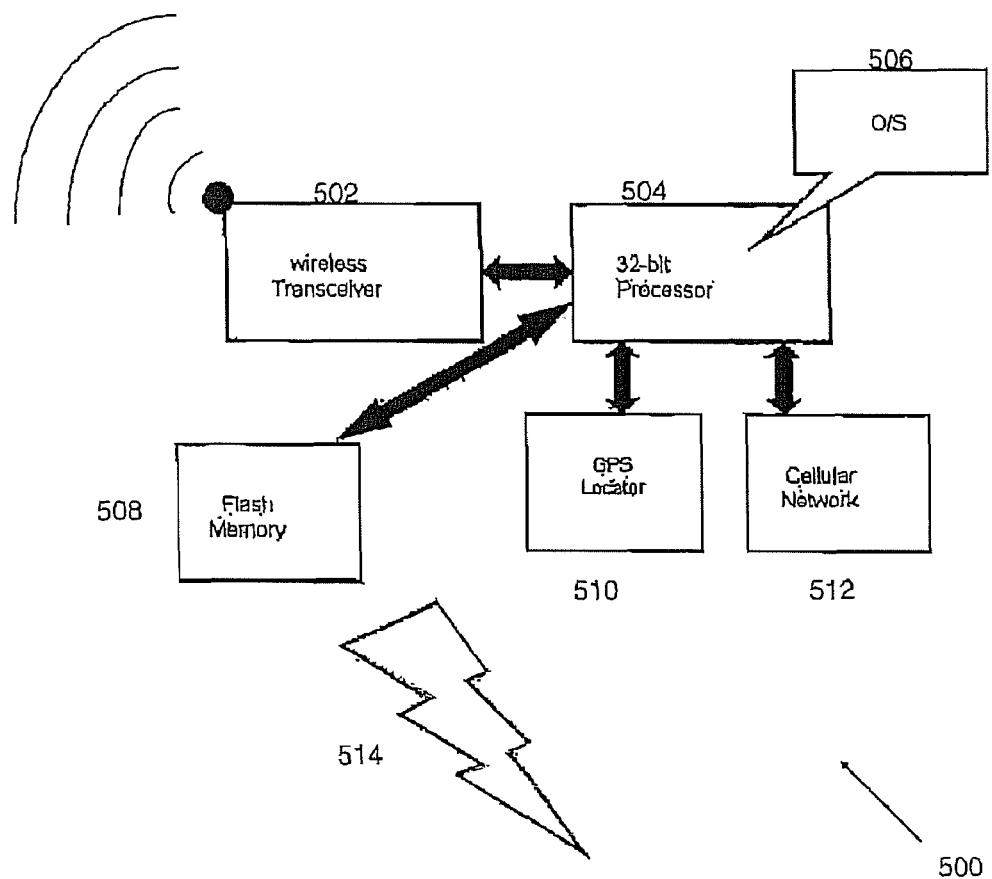
FIG. 5 shows an exemplary diagram of a mobile gateway.

In an alternative embodiment shown in FIG. 5, a mobile gateway 500 may be used in lieu of or with gateway 106. The mobile gateway 500 functions similarly to gateway 106, insofar as it can have a wireless transceiver 502 and antenna, processor 504, operating system 506 and flash memory 508. A mobile gateway 500 can also bridge the ZigBee wireless network, or any other wireless network used with the system, with a cellular network 512 and allow for monitoring of the wearer of a monitor 102 when the monitor 102 is away from their home or facility. A mobile gateway 500 can also contain GPS locator 510 capabilities to identify the location of the wearer in case of an emergency event. Further, mobile gateway 500 may use rechargeable battery 514 or an A/C source to power the device. A mobile gateway 500 may be configured in a variety of manners, such as by partnering with a mobile phone manufacturer to integrate gateway capabilities into a ZigBee-enabled, or other wireless protocol-enabled, mobile phone or by integrating gateway cellular and GPS capabilities into a wearable monitor.

Figure 6:
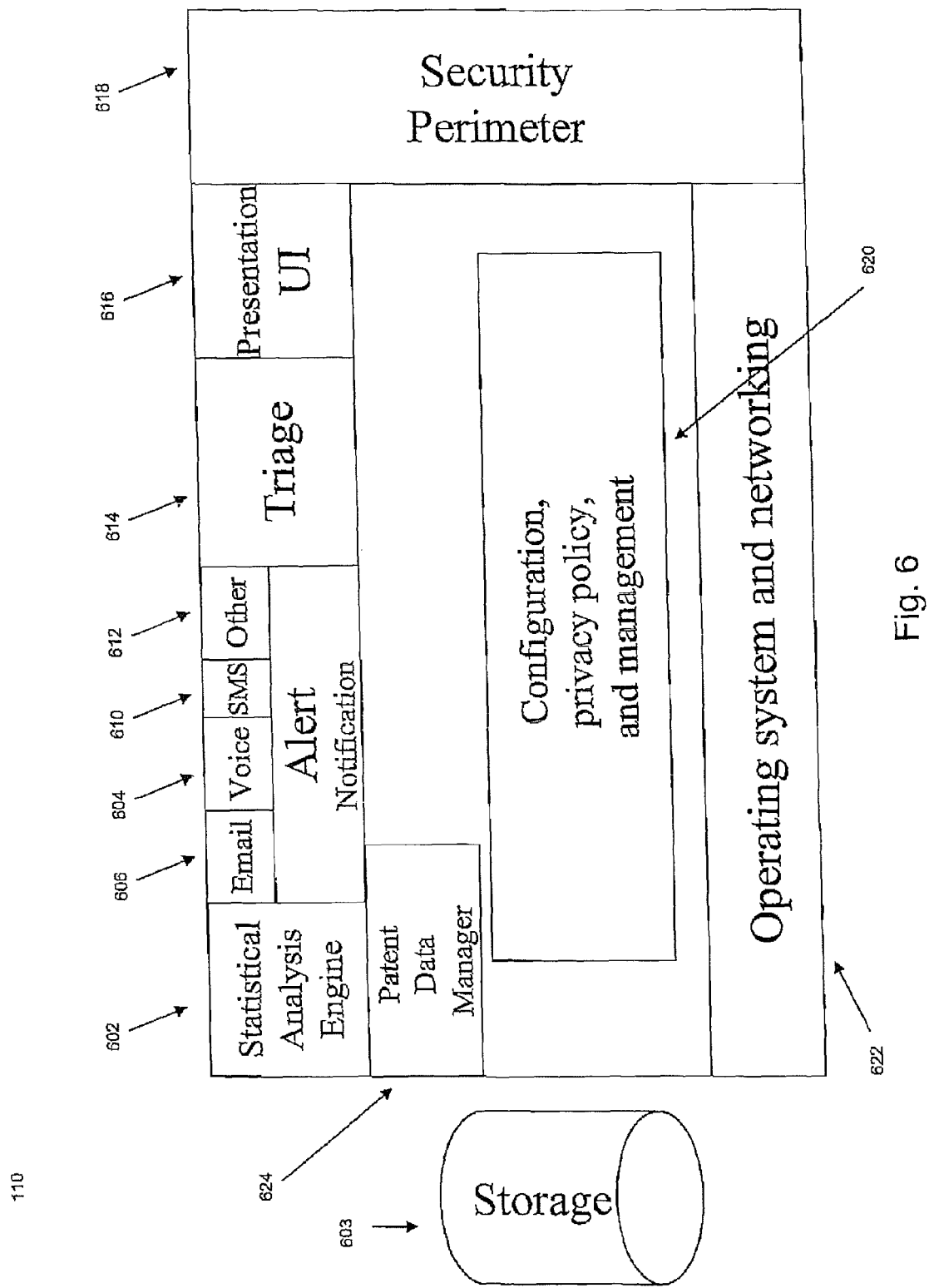
FIG. 6 shows an exemplary diagram of a server.

FIG. 6 shows a more detailed view of server 110. The server 110 can process the logic associated with the monitoring system 100 and provide the capability to configure the user information and handle the processing of events from various users using statistical analysis engine 602. Further, the server 110 can track and store the incidence of falls and other medical emergencies at the site using storage, database or databases, or memory 603 in conjunction with statistical analysis engine 602. It can also have the ability to send targeted real-time medical alerts to caregivers and may optionally escalate these alerts to additional members of a healthcare team as well as track response times using alert notification 604. These alerts may include email 606, voice transmission 608, SMS 610 or other alert transmission 612. The server 110 may also provide statistics on the vital signs of a patient or patients as well as their location and, through the use of complex applications software, can make intelligent decisions based on trends in patient data and statistical data using tools disposed in statistical analysis engine 602. Server 110 may include triage sorting capabilities 614, allowing for improved organization of patient data. A presentation user interface 616 may also be used with server 110 so as to provide an accessible and easily navigable way of viewing data in server 110 and initiating messages that are intended for monitor 102. The presentation user interface 616 may further be used by operating system and networking software 622 to provide additional methods of user access. Additionally, server 110 may have security perimeter 618, which may prevent unauthorized access to data transmitted to the server. Network configuration data, privacy information and management data 620 may also be housed on server 110. Finally, server 110 may also include patient data manager 624, which may house any of a variety of data associated with any number of patients.

The server 110 may also include one or more databases 603. Data stored in the one or more databases 603 can include accumulated patient information and system configuration information. This information can be used for a variety of purposes, such as supporting one or more remote monitors, one or gateways, one or more repeaters, and any other device that may be used in the system.

In one exemplary embodiment, at least one server may be used for deployment in support of a number of gateways, repeaters and monitors. The server, e.g. server 110, and system architecture can be flexible and scalable, however, allowing the number of servers deployed will be determined, for example, by the unique requirements presented by institutional organization, the desire by the institution for local or remote maintenance support, physical and geographic distance, network reliability, desired separation of data among multiple institutions, processing capacity desired and any other relevant needs or desires. Processing may be distributed across multiple specialized servers, which can allow, for example, certain portions of the database and complex software applications for statistics to be on one or more servers at one location, and certain portions of the database and complex software applications for communications and configuration with gateways and associated repeaters and monitors might be at another location or locations. Some deployments may include gateways, repeaters and monitors at one location but all of its supporting servers are at a different location.

The server 110 may include software bundles with rack-mounted server hardware included in operating system and networking software 622. This can be, for example, a standard Intel-based processor and PC-like functionality. Further, the server 110 associated with a deployment can have a variety of application software built on top of open source software components. Other software components can include an operating system, such as Linux, a Linux variant, Windows or a Windows-based operating system. A web-based interface, such as presentation interface 616, can also be provided via a web server, for example Apache http server. Further, an application server, such as Tomcat, can be used to dynamically monitor events and statistics and configure contact information notification services. A database may also be used to persist the configuration and data, such as patient information, contact data, and statistics. Because multiple patients, multiple monitors and multiple sensors may be included in the system, the configuration may have unique identifiers for each patient, as stored in patient data manager 624. Additionally, a set of unique messages appropriate for each type of event and each type of data from a sensor may be used. Complex software applications, such as engine 602, may utilize the data to create patient records, statistics, and analysis of data for reports. Complex software applications can also apply statistical techniques such as Bayesian Networks, moving averages, regression analysis, inference, probabilistic reasoning, and other analytical, machine learning, and artificial intelligence techniques known to a person having ordinary skill in the art to filter and apply data. Standard reports can be available on a per-event, per-patient, and per-facility basis, as well as any other desired basis. The ability to customize reports can be made available and the output from these reports could potentially also be used for billing or for quality control. Examples of open-source database projects that may be utilized are Apache projects such as Apache Derby, and mySQL or other databases known to a person having ordinary skill in the art.

The server 110 software may also include reliable queue, which can ensure scalability and reliability of the delivery of critical monitoring events to the caregiver mobile devices. Additionally, a notification service can provide the ability to communicate with mobile devices as well as the ability to send SMS text messages to pages and mobile phones as well as the sending of voice messages. The server 110 can further have the ability to process all of the events sent to it by the gateways in the facility or network and, additionally, the server 110 can have the ability to upgrade the gateway 106 as well as provide firmware to the gateway 106, which, in turn, can upgrade the wearable monitor 102 and repeater 104 components when new firmware, if desired, is available.

In another exemplary embodiment, server 110 may be able to identify specific sensor values and time stamps that originate from a specific monitor, e.g. monitor 102. This identification may be able to take place regardless of how the data from monitor 102 is transmitted or over which network path or paths the data is transmitted. For example, server 110 may identify data as being sourced from monitor 102 despite the data generated by monitor 102 having traveled over one or more of a wireless network, the Internet, a private local area network (LAN), wide area network (WAN), and a satellite or public carrier wired or wireless network. Additionally, server 110 may also account for data that may have been temporarily stored in monitor 102 when transmission was not available and later transmitted to server 110. The data sent from an exemplary monitor may include a protocol of identification and unique or specific messages and formats for the exemplary monitor. The transmitted data may include information such as values generated by sensors disposed on the monitor, the time of a sensor value, information supportive of a message error detection and correction scheme and an encryption method to protect user privacy, which may exceed HIPAA standards.

In another embodiment, server 110 may provide notification or report information on the wellness or health of a wearer of monitor 102. Server 110 may provide this information by utilizing complex application software that compares incoming data from monitor 102 with previously stored data from monitor 102 and other monitors recording similar data. Additionally, patient responses to messages sent by server 110 and displayed on monitor 102 may provide additional feedback and automatic populating of longitudinal data in databases 603 for compilation by engine 602. The comparison of the sum of the data can be used to generate predictive probabilistic statistics, for example probabilistic statistics derived from multivariate Bayesian inference networks, probabilistic relations with a deterministic predictive capability for impending events, and comparison to peers in population-based disease models. The data sourced from monitor 102 may be further be encrypted and server 110 may decrypt the data prior to processing and analyzing it. This data may also be correlated to generate notifications indicating changes in the health status of a wearer of monitor 102. Additionally, server 110 may generate location data for monitor 102 based on the network interaction and signal attributes of monitor 102, such as which devices monitor 102 is transmitting to and which network paths data generated by monitor 102 are being transmitted over.

FIG. 7 is a side view of an alternative monitor 700 that facilitates non-intrusively and more continuously detecting a user's heart beat and determining the user's heart rate. FIG. 8 is a bottom view of monitor 700. In the exemplary embodiment, monitor 700 may be a watch worn by the user on the user's wrist. Alternatively, monitor 700 may be worn on any part of the user's body, such as, but not limited to, a finger, an ankle, a thigh, a bicep, the head, the neck or the abdomen. In another embodiment, monitor 700 may be any type of bracelet, anklet and/or other wearable accessory that enables monitor 700 to function as described herein.

In the exemplary embodiment, monitor 700 may include a casing 702 coupled to a band 704 wherein a plurality of internal components may be coupled within casing 702. In one embodiment, monitor 700 may include a battery 706, an antenna 708, memory 710 and a wireless transceiver 712, which are all coupled to a processor 714. Wireless transceiver 712 facilitates communicating with server 110 and/or any other communication components of system 100. Additionally, antenna 708 facilitates producing a significantly uniform signal having a significantly uniform strength emanating in all directions. Antenna 708 may be further optimized for communication in an indoor environment. In one embodiment, processor 714 can be an ultra-low power 8-bit processor. Moreover, processor 714 may include a hibernate mode where only micro-amps of current are used to power the hibernating device, and which only "wakes up" or activates to sample data or process events, which can minimize power requirements and extend battery life. In one embodiment, memory 710 may contain the latest sensor data and alerts when monitor 700 is out of the range of a network, the protocol stack as well as firmware developed to react to events generated by the sensors.

In the exemplary embodiment, the term "processor" is not limited to just integrated circuits, but broadly refers to a microcontroller, a microcomputer, a programmable gate array, a programmable logic controller, an application specific integrated circuit and other programmable circuits. These aforementioned terms may be used interchangeably herein. As a result, processor 714 may be any type of processor known to a person having ordinary skill in the art that enables monitor 700 to function as described herein. In the exemplary embodiment, processor 714 may include a bus (not shown) or other communication mechanism for communicating information, wherein processor 714 may be coupled to the bus and facilitates processing the information. In one embodiment, a plurality of processors 714 may be arranged in a multi-processor arrangement to facilitate faster processing as compared to a single processor arrangement. In the exemplary embodiment, memory 710 may include flash memory, random access memory (RAM) or other dynamic storage device (e.g., dynamic RAM (DRAM), static RAM (SRAM) and synchronous DRAM (SDRAM)) coupled to the bus for storing information and instructions to be executed by processor 714. In addition, memory 710 may be used for storing temporary variables or other intermediate information during the execution of instructions by processor 714. Monitor 700 may further include a read only memory (ROM) or other static storage device (e.g., programmable ROM (PROM), erasable PROM (EPROM) and electrically erasable PROM (EEPROM)) coupled to the bus for storing static information and instructions for processor 714.

In addition, monitor 700 can include any of a variety of sensors such as, but not limited to, medical-grade sensors which can be employed to determine the health of the wearer. For example, the variety of sensors may include a temperature sensor (not shown) and an accelerometer 716 for the x-axis, the y-axis and the z-axis, as shown in FIG. 8 and as described in more detail below. Monitor 700 may also include a heart pulse sensor pair 718 coupled to band 704. In one embodiment, band 704 may include a plurality of sensor pairs 718 coupled thereto to form a sensor array 720. Sensor pairs 718 may be coupled to an inner surface 722 of band 704 such that when monitor 700 is coupled to the user, sensor array 720 is positioned adjacent the user's skin, and more specifically an artery of the user. Each sensor pair 718 may include an emitter 724 and a detector 726. In the exemplary embodiment, emitter 724 may include a light source 728 such as a light emitting diode (LED), which facilitates emitting light, or an electromagnetic wave into the user's body, as described in more detail below. Alternatively, light source 728 may be any type of light source known to a person having ordinary skill in the art that enables monitor 700 to function as described herein. Detector 726 facilitates detecting the light emitted into the user, which is reflected or refracted back from the user, as described in more detail below. In one embodiment, detector 726 may be a photodiode that causes varying amplitudes of current to flow in the circuit in correlation with the user's blood flow. Alternatively, detector 726 may be any type of detector known to a person having ordinary skill in the art that enables monitor 700 to function as described herein.

Each sensor pair 718 may be positioned adjacent another sensor pair 718 coupled to band 704. Adjacent sensor pairs 718 may be oriented such that emitter 724 of a first sensor pair 718 is positioned opposite from detector 726 of a second sensor pair 718 and detector 726 of the first sensor pair 718 is positioned opposite from emitter 724 of the second sensor pair 718. As a result, each sensor pair 718 is oriented in a substantially opposite position with respect to each adjacent sensor pair 718.

Figure 10:
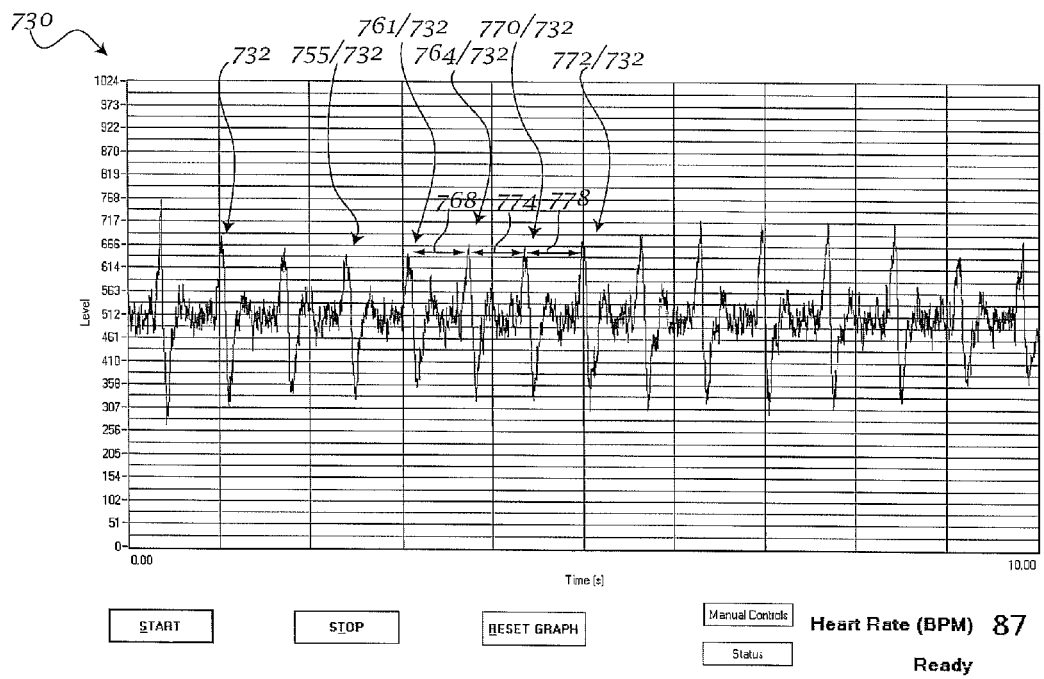
FIG. 10 shows a chart readout of a raw signal that may be detected by sensors and analyzed by the monitor shown in FIG. 7.
Figure 11:
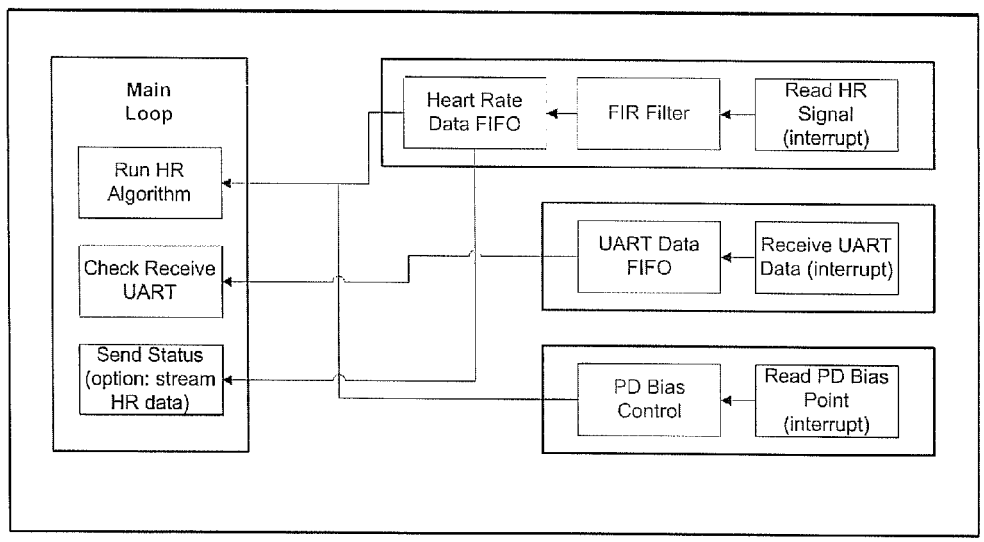
FIG. 11 shows a heart rate and heart rate variability code structure that may be used with the monitor shown in FIG. 7.
Figure 12:
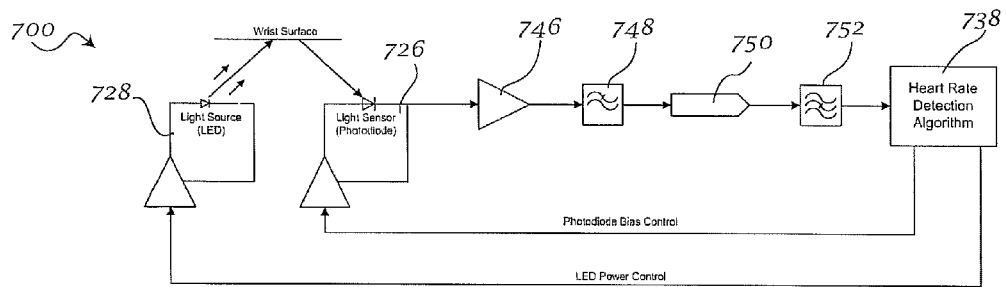
FIG. 12 shows a schematic of the monitor shown in FIG. 7.
Figure 13:
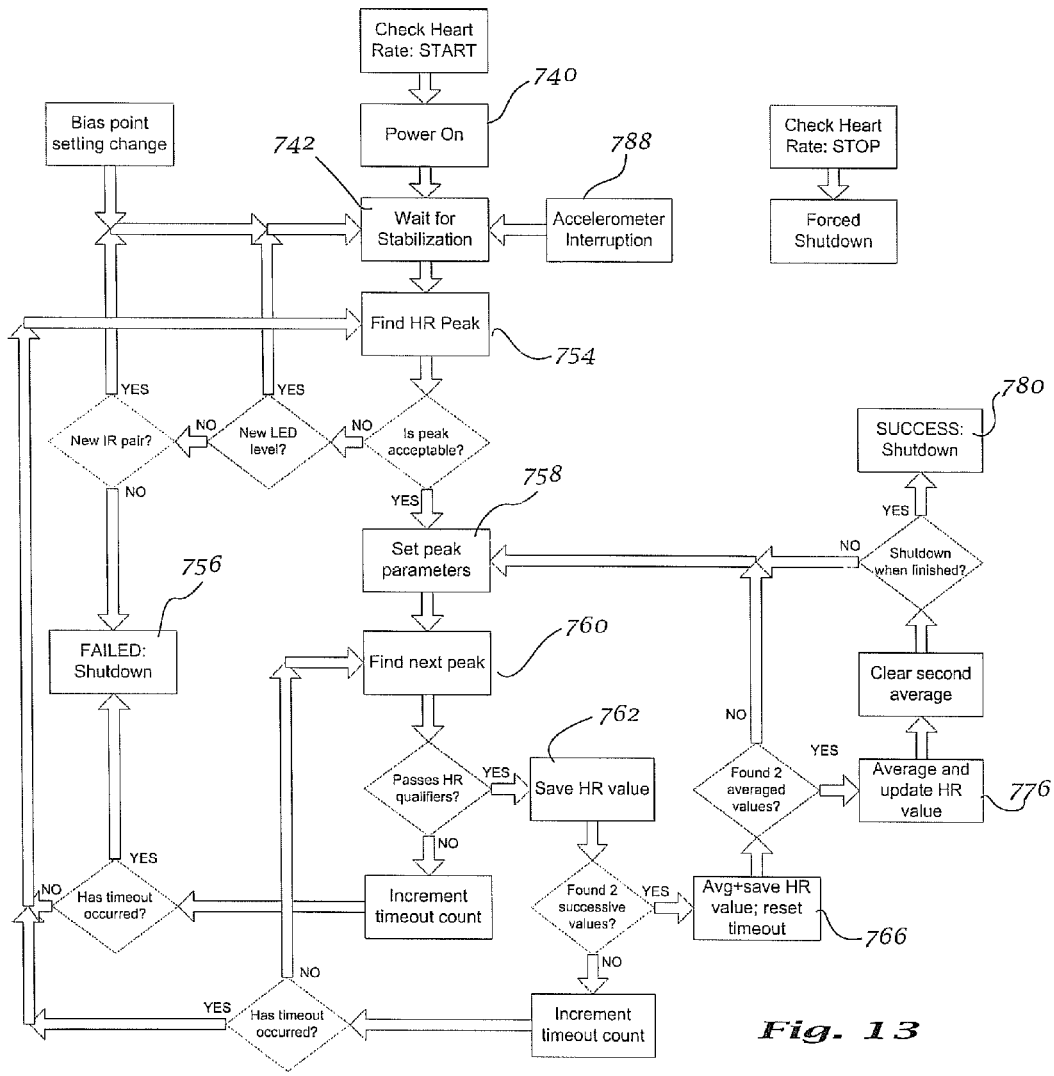
FIG. 13 shows a heart rate and heart rate variability algorithm that may be used with the monitor shown in FIG. 7.

FIG. 10 is a chart readout view of a signal 730 detected by detector 726, as described in more detail below. Signal 730 includes peak data points 732 that generally represent the user's heart beats detected by detector 726. The x-axis of the chart represents time; therefore a distance equivalent to the distance between two adjacent peak points 732 generally represents the user's heart beat interval time 734. In one embodiment, the user's heart rate is directly calculated into beats per minute; the variation between beats per minute may then be calculated into heart rate variability in the time domain. A Fourier Transform or similar technique may also be applied to the variation between beats per minute in order to transform the variation between beats per minute into the frequency domain for spectral analysis. In another embodiment, external interference and/or factors may cause artifacts, or false-positive data points to develop in the signal. Artifacts may be information or peak points that do not represent the user's heart beat but rather are caused by external factors. In one embodiment, external factors such as, but not limited to, overhead lights, fluorescent lights and the user's motion may create artifacts in the received signal 730 which may render signal 730 unreadable and unstable. Artifacts in a signal add additional peak points to the signal which monitor 700 may mistakenly confuse as a heart pulse. In such an example, if monitor 700 treats an artifact as a heart beat, monitor 700 may report incorrect vital information of the user to system 100. As a result, such artifacts should be reduced, eliminated, canceled out of the signal and/or ignored from signal 730 by monitor 700, as described in more detail below. In one embodiment, motional artifacts may be eliminated by taking a reading of the user's heart rate when the user is substantially still. In another embodiment, interference artifacts may be reduced by filtering out the known frequencies of common interfering devices such as overhead lights. In yet another embodiment, motional artifacts may be cancelled out using accelerometer 716, as described in more detail below FIG. 11 is a logic flow diagram of heart rate code structure 736 for monitor 700, which enables monitor 700 to power on, detect, for example, peak points 732 within signal 730, filter signal 730 and send a filtered signal to a heart rate algorithm 738, which facilitates determining the heart rate of the user. FIG. 12 is a schematic view of monitor 700. FIG. 13 is a logic flow chart of heart rate algorithm 738, which facilitates detecting, for example, peak points 732 in signal 730, determining the user's heart beat pulses and determining the user's heart rate.

Sensor array 720 enables monitor 700 to automatically adjust to the many different physiologies of users that may wear monitor 700. As described below, processor 714 determines which sensor pair 718 may detect an acceptable signal from the user. As a result, monitor 700 may be coupled to any type of wrist on any type of user and detect a heart beat signal.

In the exemplary embodiment, monitor 700 may be coupled to the user's wrist such that sensor array 720 is positioned substantially adjacent the underside of the user's wrist, and more specifically the user's artery. As described in more detail below, during operation, monitor 700 facilitates detecting a user's heart rate by emitting light into the skin of the user using emitter 724. The light penetrates the skin and is partially reflected or refracted back out of the skin towards detector 726. When emitter 724 is positioned substantially near an artery of the user, the pulsing of blood through the artery may selectively filter the frequency of the reflected or refracted light, such that the reflected or refracted light substantially represents the pulsing of the blood and therefore the heart beats of the user. As a result, detector 726 may detect the frequency-density changes in the reflected or refracted light, which enables monitor 700 to detect the heart beats and the heart rate of the user, as described in more detail below.

During operation, heart rate algorithm 738 powers up monitor 700 at step 740. Next, in step 742, heart rate algorithm 738 waits for stabilization of readable signal 730, wherein processor 714 searches for a readable signal 730 using sensor array 720. Stabilization of a received signal occurs when a readable heart beat signal 730 is detected by detector 726 and the heart beat signal 730 is substantially free of artifacts. Alternatively, processor 714 may use sensor array 720 to search for an optimal signal. In searching for a readable signal, monitor 700 emits light using emitter 724, wherein the light is reflected or refracted back towards monitor 700 and detected using detector 726 of one of sensor pairs 718 as signal 730. Detector 726 may need to stabilize the bias control feedback loop prior to detecting reference peaks. In one embodiment, a level of feedback may be used by monitor 700 to properly bias detector 726, which enables detector 726 to better distinguish variations in signal 730. In such an embodiment, monitor 700 may have a set or previously programmed detector bias feedback value, which is read from memory 710 by processor 714 in step 744, shown in FIG. 11. Monitor 700 then controls the detector bias feedback at step 745, which adjusts the sensitivity of detector 726. Similarly, an intensity level, or power control, of light source 728 may be adjusted by monitor 700 to facilitate increasing the effectiveness of light source 728, as described in more detail below.

In the exemplary embodiment, sensor array 720 may be coupled in communication to an analog gain 746 that facilitates increasing the analog signal before the signal is converted to a digital signal. Analog gain 746 may be coupled, in series, to an analog filter 748, an analog/digital converter 750 and a digital filter 752. In one embodiment, analog filter 748 may be a low pass filter. Analog filter 748 may also be a filter having several stages, where the first stage is about 15 Hz the second stage is about 20 Hz, and the third stage is about 66 Hz. In one embodiment, digital filter 752 may be a band stop filter or a notch filter that facilitates filtering frequencies at about 60 Hz, at about 90 Hz and at about 120 Hz. As a result, analog filter 748 and digital filter 752 facilitate removing and/or reducing ambient interference from the detected signal 730.

Turning back to FIG. 10, once signal 730 is stabilized and read by monitor 700, in step 754 heart rate algorithm 738, and more specifically processor 714, facilitates determining a reference peak point 755, which represents a reference heart beat of the user. The reference peak point 755 enables monitor 700 to determine additional heart beats of the user, though other methods of setting a reference point may also be applicable. In one embodiment, reference peak point 755 may be one of a set of potential peak points 732 within signal 730 that passes specific qualifiers, or factors, such as but not limited to, amplitude, and may be the first to be observed in the sample. A peak point 732 that has an amplitude that falls within a certain range may be an acceptable reference peak point 755. In one embodiment, the amplitude range of peak points 732 may be measured in volts. In the event signal 730 is too weak and peak points 732 have too low an amplitude, monitor 700 may automatically adjust sensor pairs 718 to facilitate enhancing signal 730. Monitor 700 may also adjust sensor pairs 718 in the event signal 730 is too strong and peak points 732 have too high an amplitude. In the case of a weak signal, monitor 700 may automatically increase the intensity of emitter 724 to facilitate strengthening the amplitude of signal 730 received by detector 726. Moreover, monitor 700 may modify the detector bias feedback to strengthen the signal detected by detector 726 to facilitate making signal 730 more readable. Similarly, monitor 700 may decrease the intensity of emitter 724 to facilitate weakening the amplitude of peak points 732 to obtain a more readable signal 730. Moreover, monitor 700 may modify the detector bias feedback to weaken the signal sensitivity of detector 726 to facilitate making signal 730 more readable.

In the event the changing of the intensity of light source 728 or changing the detector bias feedback does not produce a readable signal, monitor 700 may deactivate the current sensor pair 718 and activate another sensor pair 718 of sensor array 720. Once the new sensor pair 718 is activated, monitor 700 restarts the algorithm at step 742 and waits for stabilization. As a result, monitor 700 may fit a variety of users that have wrists of differing circumference and shape. Furthermore, monitor 700 and more specifically sensor array 720 may allow users to adjust the position of the band on their body without the need for assistance from a third party to re-position monitor 700 and sensor array 720. Monitor 700 and specifically sensor array 720 may also self-align on the user's wrist, thereby facilitating obtaining an improved signal and facilitating obtaining a signal in the event of monitor 700 being moved or adjusted by the user. As such, monitor 700, and more specifically sensor array 720 enables monitor 700 to fit virtually all users. In the event no readable signal can be found using all the sensor pairs 718 of sensor array 720, monitor 700 may turn off at shutdown step 756.

Once an acceptable reference peak point 755 is detected, monitor 700 saves the parameters of reference peak point 755 into memory 710. In one embodiment, the parameters of reference peak point 755 may include, but not limited to, amplitude. Next, in step 760 monitor 700 searches for a subsequent, or second, peak point 761 that passes specific qualifiers, such as a substantially similar amplitude as reference peak point 755 and where second peak point 761 occurs within a specific time after reference peak point 755. In the event monitor 700 detects a second peak point 761 that passes the qualifiers, second peak point 761 is saved in memory 710 as a potential first heart beat peak point in step 762. Second peak point 761 is then used as a reference peak point to enable monitor 700 to detect a third peak point 764 that passes the qualifiers with respect to second peak point 761. If third peak point 764 does not pass the qualifiers with respect to second peak point 761, then monitor 700 goes back to step 754 to begin searching for a first reference peak point 755. In other words, if third peak point 764 does not have the substantially same amplitude as second peak point 761 and/or third peak point 764 does not occur within a predicted amount of time after second peak point 761, then second peak point 761 and/or third peak point 764 may be an artifact and monitor 700 goes back to step 754 to restart the reference point process.

In step 766, if third peak point 764 passes the qualifiers, monitor 700 saves the second and third peak points 761 and 764 as heart beats and determines the time between second and third peaks points 761 and 764 to facilitate determining a first heart rate value 768. Moreover, monitor 700 saves third peak point 764 as the new reference peak point and continues searching for a subsequent fourth peak point 770 and a fifth peak point 772. Similarly, if fourth peak point 770 passes the qualifiers with respect to third peak point 764, fourth peak point 770 is then saved into memory 710 and becomes the new reference peak point for fifth peak point 772. Moreover, processor 714 may then determine a second heart rate value 774, which may be the time between third peak point 764 and fourth peak point 770.

In step 776, once forth and fifth peak points 770 and 772 are found, monitor 700 determines the time between forth and fifth peak points 770 and 772 to facilitate calculating a third heart rate value 778, which is saved to memory 710. The first, second and third heart rate values 768, 774 and 778 are then averaged together to determine an average heart rate for the user. As monitor 700 determines new heart rate values, the older heart rate values are cleared out of the averaging formula. As a result, the user's average heart rate is continually updated and the user's heart rate variability is determined. Variation in heart rate may also be determined over various time spans and may utilize statistical calculations. Furthermore, variation in heart rate may be converted to the frequency domain via utilization of Fourier Transforms, and the results of the calculation may be sent to server 110.

In one embodiment, once monitor 700 determines the heart rate of the user after detecting four uninterrupted heart beats, monitor 700 may shutdown at step 780. Alternatively, monitor 700 may be programmed to continuously detect the user's heart rate. In yet another embodiment, monitor 700 may be programmed to monitor the user's heart rate for a specific amount of time before shutting down. In such an embodiment, monitor 700 may also be programmed to restart after a specific amount of time and detect the user's heart rate. In another embodiment, monitor 700 may be programmed to monitor the user's heart rate for any amount of time. Allowing such variation in sampling methods may facilitate extending battery life of monitor 700. In one embodiment, the sensor pair 718 that was used in the most recent successful measurement may be retained in memory such that it may be used first in the next sample session, thereby shortening detection time and extending battery life of monitor 700.

Monitor 700 may transmit the user's heart rate and heart rate variability to server 110 using wireless transceiver 712. In the event monitor 700 is out of range of server 110, or any of the other communication components of system 100, monitor 700 may save the heart rate information in memory 710. Such information may be uploaded to server 110 once communication between server 110 and monitor 700 is restored.

In the exemplary embodiment, monitor 700 facilitates detecting a heart rate of the user using an easy to use and adaptive watch. Monitor 700 may be attached to any user's wrist and processor 714 will begin to search for a readable signal 730. Each user may have different physiologies, skin thicknesses, and wrist thicknesses to which monitor 700, and more specifically, sensor array 720 may adapt. In one embodiment, monitor 700 may be initially configured by a nurse or a technician to adjust, or customize the various settings on monitor 700 for the user and store those settings in memory 710. In such an embodiment, the various settings may be, but not limited to, the intensity level of light source 728, the detector bias feedback value of detector 726 and the particular sensor pair 718 that initially receives a readable signal 730. In the event monitor 700 shifts on the user's wrist or if the user removes monitor 700 and then reattaches monitor 700, monitor 700 may default to the custom settings in memory 710 to begin the search for signal 730, which facilitates reducing the time required to detect a readable signal thereby increasing the battery life of monitor 700. In the event monitor 700 has been substantially shifted on the wrist or reattached in a substantially different orientation than the initial orientation, monitor 700, and more specifically processor 714, may begin the stabilization process to find signal 730 as described above.

In another embodiment, monitor 700 may be initially attached by a user to their wrist, without the use of a nurse or technician to customize monitor 700. In such an embodiment, processor 700 may be programmed to initialize sensor array 720 and begin the stabilization process as described above. Monitor 700 may automatically adjust the settings of monitor 700, which may include but not limited to, the intensity of light source 728, the detector bias feedback value of detector 726 and the particular sensor pair 718. Once a readable signal 730 is found, monitor 700 may store the above-described settings into memory 710 to facilitate faster stabilization of signal 730 in the event monitor 700 is shifted on the user's wrist or removed and reattached in a substantially different orientation on the user's wrist, thereby facilitating quickly re-determining the user's heart rate after removal and reattachment.

Figure 14:
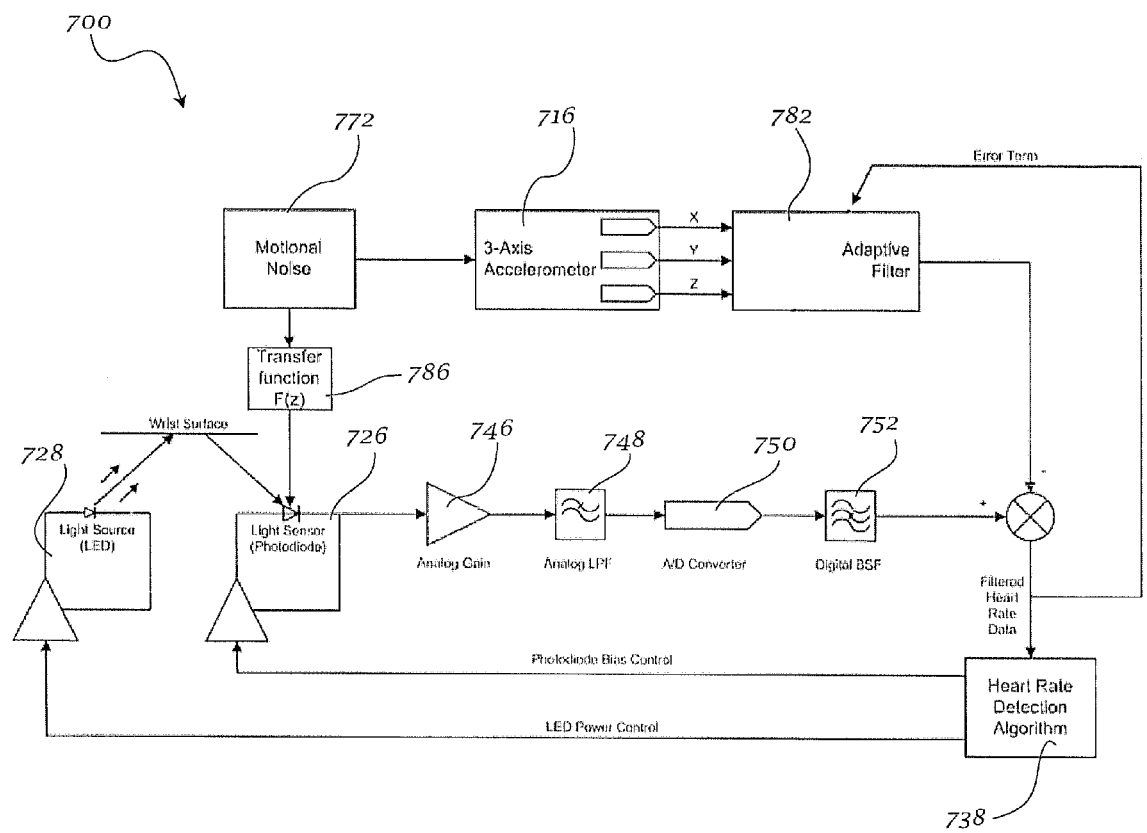
FIG. 14 shows an alternative monitor that may be used with the system shown in FIG. 1.

FIG. 14 shows an alternative embodiment of monitor 700 that includes accelerometer 716 coupled thereto. In the exemplary embodiment, accelerometer 716 facilitates measuring the acceleration, or motion, of monitor 700 in the x-axis, the y-axis and the z-axis. In the exemplary embodiment, accelerometer 716 may be coupled to an adaptive filter 782, which may utilize the information gathered by accelerometer 716 to filter undesirable heart rate artifacts due to motion.

During operation, motion of monitor 700 may create motional noise 784, which may transfer to signal 730, such that monitor 700 may detect motional noise 784. Motional noise 784 may be transferred to signal 730 such that a motional peak point generated by motional noise 784, may be a function of the motion. As a result, a transfer function 786 may be applied to the motion to determine the value of the motional peak point detected in signal 730.

In one embodiment, accelerometer 716 may be used to cancel and/or ignore motion artifacts in signal 730 that are created by the user's movements. For example, the movement of a user's arm as the user moves about may create pressure fluctuations in the user's blood flow, which may affect the reflected or refracted light which affects signal 730 received by detector 726. In one embodiment, accelerometer 716 may be used to measure the movement of monitor 700 and the movement of the user's limb to which monitor 700 is attached. Accelerometer 716 facilitates sensing and recording the movements such as, but not limited to, spatial position, acceleration and velocity of monitor 700 and the user's arm. In step 788, as shown in FIG. 13, monitor 700, and more specifically processor 714, may then match recorded motions with any received signals received at the substantially same time by detector 726. In the event a peak point is found that does not pass the qualifiers and the peak point was detected at substantially the same time as the recorded movement of monitor 700 by accelerometer 716, the peak point may be declared a motional artifact and thus ignored by processor 714. As a result, processor 714 may continue looking for a subsequent peak point without having to restart the heart rate algorithm 736, which facilitates reducing time and increasing battery life when monitor 700 determines the heart rate of the user.

In the exemplary embodiment, accelerometer 716 enables monitor 700 to detect the heart beats and determine the heart rate and heart rate variability of a user while the user is moving or walking. Motional artifacts, or changes in the user's blood flow due to the user's movement may be measured and ignored by heart rate algorithm 736. As a result, the user is more free to move about while monitor 700 monitors the user's heart rate. Moreover, accelerometer 716 reduces the need for monitor 700 to restart the stabilization process as described above, which facilitates increasing the battery life of monitor 700.

In another exemplary embodiment, transfer function 786 may adjust signal 730 in accordance with the amplitude and direction of the vector of motion. Adaptive filter 782 may also automatically approximate an unknown transfer function 786 and remove motion artifacts from signal 730. Consequently, the number of acceptable signals for the heart rate and heart rate variability algorithm may be increased, and the need for monitor 700 to continue sampling or to restart the sampling process may be reduced. This may also facilitate extending the battery life of monitor 700.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A wearable sensor comprising:
    a timing mechanism;
    a plurality of sensor pairs coupled to said timing mechanism wherein each sensor pair comprises an emitter and a detector;
    a microcontroller coupled in communication to said timing mechanism and said plurality of sensor pairs; and
    a band that facilitates coupling said plurality of sensor pairs to a user,
    wherein said plurality of sensor pairs are positioned in an array on at least one of said band and said timing mechanism, and
    wherein said microcontroller is adapted to determine which of said plurality of sensor pairs detect an acceptable signal from the user.

2. A wearable sensor in accordance with claim 1 further comprising an accelerometer coupled to said microcontroller.

3. A wearable sensor in accordance with claim 1 wherein said timing mechanism comprises a watch.

4. A wearable sensor in accordance with claim 1 wherein said emitter comprises a light emitting device.

5. A wearable sensor in accordance with claim 1 wherein said detector comprises a photodiode.

6. A monitoring system, comprising:
    at least one wearable monitor coupled to a user, said at least one wearable monitor comprising:
    a timing mechanism;
    a plurality of sensor pairs coupled to said timing mechanism wherein each sensor pair comprises an emitter and a detector; and
    a microcontroller coupled in communication to said timing mechanism and said plurality of sensor pairs;
    at least one gateway having a second transceiver;
    at least one device located at a remote location; and
    at least one server coupled in communication using a wide area network to the at least one gateway and the at least one device, said at least one wearable monitor is coupled in wireless communication to said at least one gateway, said plurality of sensor pairs facilitate sensing a heart rate of the user and transmit the heart rate to said at least one server; and
    a band that facilitates coupling said plurality of sensor pairs to a user,
    wherein said plurality of sensor pairs are positioned in an array on at least one of said band and said timing mechanism, and
    wherein said microcontroller is adapted to determine which of said plurality of sensor pairs detect an acceptable signal from the user.

7. A system in accordance with claim 6 further comprising an accelerometer coupled to said microcontroller, said accelerometer facilitates detecting movement of said wearable sensor.

8. A system in accordance with claim 6 wherein said timing mechanism comprises a watch.

9. A system in accordance with claim 6 wherein said emitter comprises a light emitting device.

10. A system in accordance with claim 6 wherein said detector comprises a photodiode.

11. A method of sensing a heart rate using a wearable monitor, said wearable monitor comprising:
    a timing mechanism;
    a memory;
    a plurality of sensor pairs coupled to the timing mechanism wherein each sensor pair comprises an emitter and a detector;
    a microcontroller coupled in communication to the timing mechanism, the memory and the plurality of sensor pairs; and
    a band that facilitates coupling said plurality of sensor pairs to a user,
    wherein said plurality of sensor pairs are positioned in an array on at least one of said band and said timing mechanism, and
    wherein said microcontroller is adapted to determine which of said plurality of sensor pairs detect am the user,
    said method comprising:
        coupling the wearable monitor to a user;
        emitting an electromagnetic wave from the emitter into the user;
        receiving an electromagnetic wave signal from the user at the detector;
        stabilizing the electromagnetic wave;
        determining a first pulse;
        determining a plurality of subsequent pulses;
        calculating a heart rate of the user; and
        recording the heart rate of the user in at least one server.

12. A method in accordance with claim 11 wherein stabilizing the electromagnetic wave further comprises:
    filtering ambient electromagnetic waves; and
    biasing the detector to facilitate receiving a readable electromagnetic wave signal.

13. A method in accordance with claim 11 wherein determining a first pulse further comprises:
    sensing a first peak amplitude in the electromagnetic wave signal using a first sensor pair;
    determining whether the first peak amplitude is acceptable;
    adjusting an electromagnetic wave emission level of the emitter in the event the peak amplitude is not acceptable;
    sensing the first peak amplitude in the electromagnetic wave signal using a second sensor pair in the event the first sensor pair cannot sense an acceptable peak amplitude;
    recording a first acceptable peak amplitude in the memory of the wearable monitor; and
    recording the most recently used sensor pair in the memory of the wearable monitor.

14. A method in accordance with claim 13 wherein determining a plurality of subsequent pulses further comprises:
    sensing at least three subsequent peak amplitudes in the signal using the same sensor pair that detected the first acceptable peak amplitude, wherein each subsequent peak amplitude is within an acceptable range with respect to the preceding peak amplitude; and
    recording the at least three subsequent peak amplitudes in the memory of the wearable monitor.

15. A method in accordance with claim 14 wherein calculating a heart rate of the user further comprises:
recording the time between each peak amplitude to determine the instantaneous heart rate of the user; and
averaging the recorded times between peak amplitudes to determine the average heart rate of the user.

16. A method in accordance with claim 15 wherein calculating a heart rate of the user further comprises:
calculating statistical variation in heart rate over time;
using Fourier Transforms to transform variations in the instantaneous heart rate of the user into a frequency domain for spectral analysis of heart rate variation.

17. A method in accordance with claim 11 wherein determining a first pulse further comprises:
detecting movements of the wearable monitor caused by the movements of the user using an accelerometer that is coupled to the microcontroller;
determining false-positive peak amplitudes that coincide with movements of the wearable monitor detected by the accelerometer; and
omitting the false-positive peak amplitudes from said step of calculating a heart rate such that the wearable monitor may sense the heart rate of the user while the user is moving.

18. A method in accordance with claim 17 wherein determining a first pulse further comprises:
increasing the occurrence of acceptable peak amplitudes by mathematically compensating peak amplitudes based on the amplitude and direction of the movements of the user.

19. A health care monitoring system comprising:
means for emitting electromagnetic waves into a user;
means for receiving the emitted electromagnetic waves as a signal;
means for determining a plurality of peak amplitudes within the signal;
means for calculating a heart rate of the user;
means for recording the heart rate on at least one server; and
means for sensing the electromagnetic waves using a second sensor pair in the event a first sensor pair cannot sense an acceptable peak amplitude.

20. A health care monitoring system in accordance with claim 19 further comprising means for filtering ambient electromagnetic waves.

21. A health care monitoring system in accordance with claim 19 further comprising means for omitting false-positive peak amplitudes in the signal caused by the movements of the user.

22. A health care monitoring system in accordance with claim 19 further comprising means for increasing the occurrence of acceptable peak amplitudes by mathematically compensating peak amplitudes based on the amplitude and direction of the movements of the user.

* * * * *